United States Patent
Terry

(10) Patent No.: US 7,378,156 B2
(45) Date of Patent: May 27, 2008

(54) ANTIMICROBIAL COMPOSITIONS CONTAINING COLLOIDS OF OLIGODYNAMIC METALS

(75) Inventor: Richard Terry, Conyers, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 11/625,038

(22) Filed: Jan. 19, 2007

(65) Prior Publication Data

US 2007/0218298 A1    Sep. 20, 2007

Related U.S. Application Data

(63) Continuation of application No. 10/649,595, filed on Aug. 26, 2003, now Pat. No. 7,179,849, which is a continuation-in-part of application No. 09/461,846, filed on Dec. 15, 1999, now Pat. No. 6,716,895.

(60) Provisional application No. 60/405,936, filed on Aug. 26, 2002, provisional application No. 60/406,343, filed on Aug. 26, 2002, provisional application No. 60/406,384, filed on Aug. 26, 2002, provisional application No. 60/406,496, filed on Aug. 28, 2002, provisional application No. 60/406,497, filed on Aug. 28, 2002.

(51) Int. Cl.
*B32B 27/40* (2006.01)
(52) U.S. Cl. .................... 428/425.9; 428/423.1
(58) Field of Classification Search ............. 428/423.1, 428/425.9
See application file for complete search history.

(56) References Cited

U.S. PATENT DOCUMENTS

| | | | |
|---|---|---|---|
| 5,788,687 A | 8/1998 | Batich et al. | |
| 5,848,995 A | 12/1998 | Walder | |
| 6,579,539 B2 | 6/2003 | Lawson | |
| 6,596,401 B1 * | 7/2003 | Terry et al. | 428/447 |
| 6,669,981 B2 | 12/2003 | Parsons et al. | |
| 7,087,249 B2 | 8/2006 | Burrell et al. | |
| 7,179,849 B2 | 2/2007 | Terry | |

OTHER PUBLICATIONS

PCT/US2007/63180, Terry R., filed Mar. 2, 2007.

* cited by examiner

*Primary Examiner*—D. S Nakarani
(74) *Attorney, Agent, or Firm*—Greenblum & Bernstein, P.L.C.

(57) ABSTRACT

The present invention relates to antimicrobial compositions, methods for the production of these compositions, and use of these compositions with medical devices, such as catheters, and implants. The compositions of the present invention advantageously provide varying release kinetics for the active ions in the compositions due to the different water solubilities of the ions, allowing antimicrobial release profiles to be tailored for a given application and providing for sustained antimicrobial activity over time. More particularly, the invention relates to polymer compositions containing colloids comprised of salts of one or more oligodynamic metal, such as silver. The process of the invention includes mixing a solution of one or more oligodynamic metal salts with a polymer solution or dispersion and precipitating a colloid of the salts by addition of other salts to the solution which react with some or all of the first metal salts. The compositions can be incorporated into articles or can be employed as a coating on articles such as medical devices. Coatings may be on all or part of a surface.

14 Claims, 5 Drawing Sheets

ANTIMICROBIAL COMPOSITIONS CONTAINING COLLOIDS OF OLIGODYNAMIC METALS

PRIOR RELATED APPLICATIONS

This application is a continuation on of U.S. patent application Ser. No. 10/649,595, filed Aug. 26, 2003 now U.S. Pat. No. 7,179,849, allowed, which is a continuation-in-part application of U.S. patent application Ser. No. 09/461,846, filed Dec. 15, 1999, now U.S. Pat. No. 6,716,895. This application also claims the benefit of U.S. provisional patent application Ser. No. 60/405,936, filed Aug. 26, 2002, U.S. provisional patent application Ser. No. 60/406,343, filed Aug. 26, 2002, U.S. provisional patent application Ser. No. 60/406,384, filed Aug. 26, 2002, U.S. provisional patent application Ser. No. 60/406,496, filed Aug. 28, 2002, and U.S. provisional patent application Ser. No. 60/406,497, filed Aug. 28, 2002.

FIELD OF THE INVENTION

The present invention relates generally to polymer compositions and their use for making or coating articles, such as medical devices. More specifically the invention relates to antimicrobial compositions containing a polymer and oligodynamic salts. Further, the present invention relates to compositions containing active agents as well as oligodynamic salts and their use.

BACKGROUND OF THE INVENTION

For many years silver and silver salts have been used as antimicrobial agents. An early medicinal use of silver was the application of aqueous silver nitrate solutions to prevent eye infection in newborn babies. Silver salts, colloids, and complexes have also been used to prevent and to control infection. For example, colloidal metallic silver has been used topically for conjunctivitis, urethritis, and vaginitis.

Other metals, such as gold, zinc, copper, and cerium, have also been found to possess antimicrobial properties, both alone and in combination with silver. These and other metals have been shown to provide antimicrobial behavior even in minute quantities, a property referred to as "oligodynamic."

Additionally, silver is known for antimicrobial use with medical devices, such as catheters, cannulae, and stents. One conventional approach for obtaining antimicrobial medical devices is the deposition of metallic silver directly onto the surface of the substrate, for example, by vapor coating, sputter coating, or ion beam coating. However, these non-contact deposition coating techniques suffer many drawbacks. These drawbacks include poor adhesion, lack of coating uniformity, and the need for special processing conditions, such as preparation in darkness due to the light sensitivity of some silver salts. One particular drawback of these coatings is that the processes by which the coatings are formed do not adequately coat hidden or enclosed areas, such as the interior lumen of a catheter or stent. Additionally, these methods produce coatings that are very much like metallic silver in that they do not release silver from the coating and require contact with the coating to provide antimicrobial action. Though high concentrations of silver may be deposited on the substrate, very little free ionic silver is released on exposure to aqueous fluid. As a result, these coatings provide only limited antimicrobial activity. They essentially retard colonization of microbial agents on the surface of the device. However, because they do not release sufficient silver ions into aqueous fluids, they offer little or no protection from bacteria carried into the body upon insertion of the device and do not inhibit infection in the surrounding tissue.

Another method of coating silver onto a substrate involves deposition or electrodeposition of silver from solution. Drawbacks of these methods include poor adhesion, low silver pick-up on the substrate, the need for surface preparation, and high labor costs associated with multistep dipping operations usually required to produce the coatings. Adhesion problems have been addressed by inclusion of deposition agents and stabilizing agents, such as gold and platinum metals, or by forming chemical complexes between a silver compound and the substrate surface. However, inclusion of additional components increases the complexity and cost of producing such coatings.

With many medical devices, it is preferred to have a lubricious coating on the device. Lubricious coatings aid device insertion, reduce the trauma to tissue, and reduce the adherence of bacteria. Another drawback to conventional methods which apply silver and other metals directly onto the surface of a medical device for which a lubricious coating is also desired is that a second, lubricious coating must be applied to the device over the antimicrobial coating, adding to manufacturing cost and time.

Some of these coatings release, to varying degrees, silver ions into the solution or tissue surrounding the substrate. However, activation of such coatings often requires conditions that are not suitable for use with medical implants, such as catheters, stents, and cannulae. These conditions include abrasion of the coating surface, heating to a temperature above 180° C., contact with hydrogen peroxide, and treatment with an electric current.

Another conventional approach for obtaining antimicrobial medical devices is the incorporation of silver, silver salts, and other antimicrobial compounds into the polymeric substrate material from which the article is formed. An oligodynamic metal may be physically incorporated into the polymeric substrate in a variety of ways. For example, a liquid solution of a silver salt may be dipped, sprayed or brushed onto—the solid polymer, for example, in pellet form, prior to formation of the polymeric article. Alternatively, a solid form of the silver salt can be mixed with a finely divided or liquefied polymeric resin, which is then molded into the article. Further, the oligodynamic compound can be mixed with monomers of the material prior to polymerization.

There are several disadvantages to this approach. One such disadvantage is that larger quantities of the oligodynamic material are required to provide effective antimicrobial activity at the surface of the device. A second disadvantage is that it is difficult to produce articles that allow for the release of the oligodynamic material because most device polymers absorb little, if any, water to aid in the diffusion and release of the oligodynamic material, resulting in articles that provide only a limited antimicrobial effect.

Yet another approach for obtaining antimicrobial medical devices is the incorporation of oligodynamic agents into a polymeric coating which is then applied to the surface of the article. Typically, an oligodynamic agent is incorporated into the coating solution in the form of a solution or a suspension of particles of the oligodynamic agent. Problems associated with this approach include poor adhesion of the coating to the substrate, settling and agglomeration of the oligodynamic particles, and inadequate antimicrobial activity over time.

Settling of particles of the oligodynamic agent occurs as a result of the size and density of the particles. Settling of the particles from such solutions can cause unpredictable changes in the concentration of the oligodynamic agent in the composition. These changes in concentration result in several drawbacks to producing commercial products. First, unpredictable changes in the concentration of the oligodynamic agent make it difficult to produce a composition having a specific concentration of antimicrobial ions and, thus, a particular effectiveness. Additionally, these changes make it difficult to produce multiple batches of the composition having the same antibacterial concentration. Further, the concentration of the antimicrobial ions can affect other properties of the composition, such as its adhesive and lubricious properties. Consistency of antimicrobial activity is essential in the production of medical devices.

Another problem associated with particle suspensions is agglomeration of the particles. Particle agglomeration produces larger particle sizes which increases settling of particles from solution. Additionally, the agglomeration of particles in suspensions and coating solutions can produce particles in the coating that are large enough to be noticeable to the touch on the coated surface. Articles produced using such coatings have decreased patient comfort and, therefore, are undesirable.

Many researchers have attempted to overcome these problems. For example, U.S. Pat. No. 4,592,920 to Murtfeldt et al. discloses a process that attempts to overcome the settling and agglomeration problems in the art through the use of a comminuted metal having a particle size of 30 microns or less. The coating of the Murtfeldt patent, however, exhibits several disadvantages. For example, the Murtfeldt coating exhibits poor adhesion which is overcome by the use of the following methods. First, the Murtfeldt patent recommends pretreatment of the catheter to leach undesirable compounds that interfere with the bonding of the coating to the surface of the catheter. Second, the Murtfeldt patent recommends the use of a bridging compound, or primer, to attach the coating to the surface of the catheter to increase adhesion. This adds an additional manufacturing step to the fabrication of a coated device. In addition to these disadvantages, it is likely that the process used to manufacture and coat the catheters in Murtfeldt will result in settling and agglomeration problems even with the use of silver having smaller particle sizes.

U.S. Pat. No. 4,849,223 to Pratt et al. attempts to overcome settling and agglomeration of the particles in his invention by using solutions that contain high concentrations of polymer or monomer solids and are, thus, viscous. Suspending particles in high viscosity coating solutions containing high polymer solids is a common method for reducing settling and agglomeration of the particles. The coatings made by this method are usually very thick and, as a result, are often not uniform. Thick coatings are also more costly, dry more slowly than thin coatings, and are more difficult to manufacture. The coatings of the Pratt patent also exhibit poor adhesion. To increase adhesion, the Pratt patent recommends using coating materials which are similar to the substrate to be coated, pretreating the surface of the substrate before the coating composition is applied, or applying an additional coating layer between the substrate and the coating.

U.S. Pat. No. 5,019,096 to Fox, Jr. et al. discloses a method for increasing the antibacterial activity of silver by incorporating a synergistic amount of chlorhexidine and a silver salt in a matrix-forming polymer. The polymer is such that it allows for release of the antimicrobial agent over an extended period of time. Fox, however, relies on dispersation of silver particles into coating solutions and will be susceptible to problems associated with particle settling and agglomeration.

U.S. Pat. No. 4,677,143 to Laurin et al. discloses a method to enhance release of the antimicrobial metal ions from the surface of a device by incorporating the antimicrobial metal into a binder having a low dielectric constant that coats or forms the device. The nature of the binder allows the particles to form chain-like structures among themselves. These chain-like structures allow the surface particles to dissolve to provide an initial dose of the antimicrobial agent and to create a pathway for interior particles to come to the surface to provide additional doses of the antimicrobial agent over time. Laurin, however, also relies on dispersation of silver particles into coating solutions and is susceptible to problems associated with particle settling and agglomeration.

U.S. Pat. No. 4,933,178 to Capelli discloses a polymer coating containing an oligodynamic metal salt of a sulfonylurea. The Capelli patent attempts to improve the solubility and stability of the antimicrobial metal in the coating and to provide for the sustained release of the antimicrobial agent by adding a carboxylic acid to the coating composition. The particular carboxylic acids and the proportions in which they are mixed determine the rate of release of the antimicrobial agent from the polymer coating composition.

U.S. Pat. No. 5,848,995 to Walder discloses the solid phase production of polymers containing AgCl as an antimicrobial agent. In the Walder process, solid polymer pellets are first soaked in a solution of silver nitrate which is absorbed into the pellets. The pellets are then rinsed, dried, and soaked in a solution of a sodium chloride. The chloride ions of the salt are absorbed into the polymer matrix of the pellets where they react with the silver nitrate to form silver chloride. The pellets are then rinsed, dried, and melt processed. The compositions of the Walder patent are limited to hydrophilic polymers, must be thermoformed, and do not contain other silver salts to provide multiple release rates, or other oligodynamic or medicinal agents to enhance antimicrobial effectiveness.

Therefore, there is a need in the art to provide a method for rendering articles, such as medical devices, resistant to infection, on the surface of the article, in tissue surrounding articles, or in both locations. There is also a need in the art for compositions which can be incorporated into articles to provide antimicrobial activity. Further, there is a need for compositions which can be employed as coatings for articles that exhibit improved adhesion. There is also a need for compositions that overcome the solubility, settling, and agglomeration problems of conventional oligodynamic compositions, and exhibit enhanced, sustained release of oligodynamic agents. There is further a need for compositions that allow delivery of one or more active agents to locations.

SUMMARY OF THE INVENTION

Stated generally, the present invention comprises antimicrobial compositions which in a first aspect provide the advantage of reduced settling and agglomeration by producing a minimal particle size of the oligodynamic salts in the compositions. The use of colloids in the compositions also permits incorporation of higher quantities of antimicrobial ions without the difficulties associated with the suspensions used in the prior art.

In another aspect, the compositions of the present invention provide the advantage of varying release kinetics for the active oligodynamic ions due to the different water solubilities of the different salts in the compositions. These varying release kinetics allow for an initial release of oligodynamic ions that provides antimicrobial activity immediately upon insertion, followed by a continual, extended release of the oligodynamic ions from the composition, resulting in sustained antimicrobial activity over time.

Stated somewhat more specifically, the present invention relates in one aspect to compositions that comprise a polymer and a colloid containing salts of one or more oligodynamic agents. In one disclosed embodiment, the polymer is a hydrophilic polymer. In another disclosed embodiment, the polymer is a hydrophobic polymer, while in yet another embodiment, the polymer is a combination of these two types of polymers.

In one disclosed embodiment, the invention comprises one or more salts of silver as the oligodynamic agent. In another embodiment, the composition optionally contains additional salts of other oligodynamic metals, such as zinc, gold, copper, cerium and the like. In yet another embodiment, the composition optionally comprises additional salts of one or more noble metals to promote galvanic action. In still another embodiment, the composition optionally comprises additional salts of platinum group metals such as platinum, palladium, rhodium, iridium, ruthenium, osmium, and the like.

In a further aspect, the compositions optionally contain other components that provide beneficial properties to the composition, that improve the antimicrobial effectiveness of the composition, or that otherwise serve as active agents to impart additional properties to the compositions.

In another aspect, the present invention relates to a process for producing these antimicrobial compositions. The process comprises the formation of colloids of oligodynamic agents in solutions, dispersions, or combinations of polymers solutions and dispersions. The terms "polymer composition" and "polymer solution" are used interchangeably throughout the specification and claims and both means any polymer solution, dispersion, or combination of polymer solutions and dispersions. The colloid can be formed first and then added to the polymer composition or can be formed in situ in the polymer composition. Preferably, the colloid is formed in situ in the polymer composition.

The process of forming the colloids comprises, for example, combining two or more salts, wherein at least one of the salts is the salt of an oligodynamic agent. These salts will be referred to herein as salt A and salt B. Salt A comprises one or more oligodynamic agents. Salt B comprises one or more salts that can react with salt A to form a colloid. Salts A and B can be combined in any amount and in any order. In some embodiments, it is preferred that salt A be present in a stoichiometric amount or in excess when compared to salt B. In some embodiments, it is preferred that salt B be present in a stoichiometric amount or in excess when compared to salt A.

Optionally, additional components can be added to the antimicrobial compositions of the present invention. These components include, but are not limited to, additional oligodynamic agents, additional soluble salts, salts which provide galvanic action, and any other components which provide the compositions with beneficial properties or enhance the antimicrobial activity of the compositions. Such components include, but are not limited to, antimicrobial agents, antibiotics, and other medicinal agents.

In one disclosed embodiment, the antimicrobial composition of the invention is produced by forming a solution, dispersion, or combination of solutions and dispersions of one or more polymers. Next, a solution comprising salt A is added to the polymer composition. Then, a solution comprising salt B is added to the polymer composition to precipitate fine colloidal salt(s) of the oligodynamic agent(s). Where the oligodynamic agent is a metal salt, the metal cation of salt A reacts with the anion of salt B to form a less soluble salt which precipitates as a fine colloid. Salt B is added to the polymer composition in an amount sufficient to react with some or all of salt A. Optionally, other salts are then added in amounts to react with some or all of the remaining amount of salt A.

In another disclosed embodiment, salt B is added to the polymer composition, followed by the addition of an excess or stoichiometric amount of salt A. In yet another embodiment, salts A and B can be combined to form a colloid which is then added to the polymer composition.

The final polymer composition formed by these processes contains one or more colloidal salts, composed of the oligodynamic cations of salt A and the anions of salt B, and one or more soluble salts, composed of the anions of salt A and the cations of salt B.

The compositions are used to coat substrate materials. Thus, another aspect of the invention is a coating containing the composition of the invention. These coatings may comprise either a single layer or multiple layers. The compositions of the present invention are used alone or in combination with other polymer coatings to provide advantageous properties to the surface of the substrate. These compositions are used, for example to deliver pharmaceutical agents that, for example, prevent infection, reduce encrustation, inhibit coagulation, improve healing, inhibit restenosis, or impart antiviral, antifungal, antithrombogenic or other properties to coated substrates.

The compositions are also used to inhibit algae, fungal, mollusk, or microbial growth on surfaces. The compositions of the invention are also used as herbicides, insecticides, antifogging agents, diagnostic agents, screening agents, and antifoulants.

In another aspect, the present invention relates to an article of manufacture which comprises the antimicrobial compositions of the present invention. In one embodiment, the composition is used to form an article or a portion of the article, for example by molding, casting, extrusion, etc. Thus, at least part of the formed article is composed of one or more of the compositions of the present invention, alone or in admixture with other polymeric components. In another disclosed embodiment, the composition is applied to a preformed article or part of an article as a coating. The coated article may be produced, for example, by dipping the article into the composition or by spraying the article with the composition and then drying the coated article. In a preferred embodiment, the compositions are used to coat medical devices.

It is therefore an object of the present invention to provide compositions containing a polymer and a colloid wherein the colloid contains a salt or oxide of an oligodynamic metal.

It is another object of the present invention to provide compositions that provide antimicrobial, antibacterial, antiviral, antifungal, or antibiotic activity or some combination thereof.

It is another object of the present invention to provide compositions that, reduce encrustation, inhibit coagulation, improve healing, inhibit restenosis, or impart antiviral, antifungal, antithrombogenic or other properties to coated substrates.

It is yet another object of the present invention to provide herbicidal or insecticidal compositions.

It is an object of the present invention to provide compositions that inhibit the growth of algae, mollusks, bacterial, bioslime, or some combination thereof on surfaces.

It is a further object of the present invention to provide compositions for the delivery of active agents including, but not limited to, pharmaceutical or therapeutic agents, growth factors, cytokines, or immunoglobulins. It is yet another object of the invention to provide compositions that comprise a silane copolymer and a biguanide.

It is a further object of the present invention to provide compositions that comprise a silane copolymer and chlorhexidine or a salt of chlorhexidine.

It is another object of the present invention to provide compositions that comprise a silane copolymer and an antibiotic.

It is yet another object of the present invention to provide topical compositions for the delivery of pharmaceutical agents.

It is a further object of the present invention to provide compositions for the delivery of growth factors, cytokines, or immunoglobulins.

It is a further object of the present invention to provide articles comprising the compositions of the invention including, but not limited to articles formed in whole or in part of the compositions and articles coated in whole or in part with the compositions.

It is a further object of the present invention to provide methods of making the compositions of the invention.

It is a further object of the present invention to provide methods of making the articles of the invention.

It is a further object of the present invention to provide methods of coating articles with the composition of the invention.

DETAILED DESCRIPTION OF THE PREFERRED EMBODIMENTS

The Composition

Figure 1:
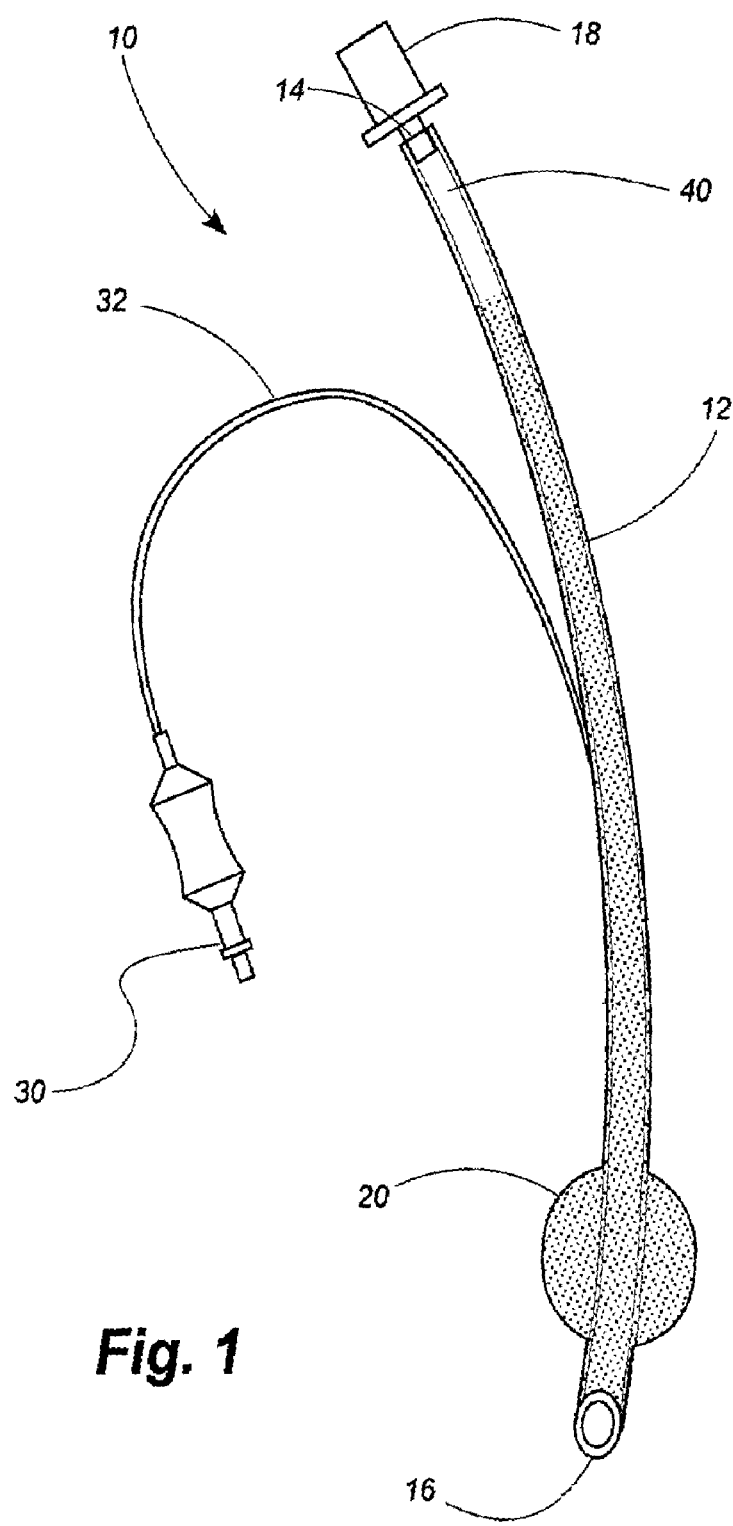
FIG. 1 depicts an endotracheal tube partially coated with a coating of the present invention. Part of the tube is not coated.

In a first aspect, the present invention provides antimicrobial compositions. The compositions comprise a polymer and a colloid comprised of the salts of one or more oligodynamic agents. The term "oligodynamic agents" as used in the present invention refers to any compound that can provide antimicrobial activity, even when present in small quantities.

Any polymer may be employed in the present invention, including hydrophilic polymers, hydrophobic polymers, and mixtures of these two types of polymers. The use of hydrophilic polymers is preferred because such polymers have additional benefits. These benefits include increased lubricity for patient comfort, increased absorption of aqueous fluids from the body which aids in the release of oligodynamic ions from the composition, inhibition of bacterial attachment, and improved solubility for some metal salts. Hydrophilic polymers best suited to the invention are those that are soluble in water or in organic solvents containing water. The ability to add water to the polymer composition without precipitating the polymer facilitates the addition of water-soluble salts directly to the coating composition. Water facilitates the formation of salt colloids within the polymer composition. For this reason, it is preferred that the polymer solution contain from 1 to 50% water by weight, more preferably from 5 to 30% water by weight.

However, the use of water is not limiting, as salt colloids can also be formed using alcohols, organic solvents, or both that contain little or no water. The use of alcohols and organic solvents, containing from 0 to 1% water are preferred when hydrophobic polymers are employed in the present invention.

Examples of polymers which may be used to form the compositions include, but are not limited to, polyurethanes, including polyether polyurethanes, polyester polyurethanes, polyurethaneureas, and their copolymers; polyvinylpyrrolidones; polyvinyl alcohols; polyethylene glycols and their copolymers; polypropylene glycols and their copolymers; polyoxyethylenes and their copolymers; polyacrylic acid; polyacrylamide; carboxymethyl cellulose; glycoproteins; proteoglycans; glycosaminoglycans; lipoproteins; liposaccharides; cellulose and its derivatives; dextrans and other polysaccharides; starches; guar; xantham and other gums and thickeners; collagen; gelatins; other naturally occurring polymers; polytetrafluoroethylene; polyvinyl chloride (PVC); polyvinylacetate; poly(ethylene terephthalate); silicone; polyesters; polyamides; polyureas; styrene-block copolymers; polymethyl methacrylate; acrylic-butadiene-styrene copolymers; polyethylene; polystyrene; polypropylene; natural and synthetic rubbers; acrylonitrile rubber; and mixtures and copolymers of any of the above. The preferred polymer depends upon the substrate to be coated. In some preferred, the polymer is a polyurethanes and polyurethane copolymers, such as polyether polyurethaneurea. In some embodiments, hydrophobic polymers that are chemically similar or identical to the substrate are used alone or in combination with hydrophilic polymers to form coatings that enhance adhesion of the coating to the substrate.

The colloid of the present invention comprises one or more oligodynamic salts. In the discussion of the process below, the oligodynamic metal cations come from the salts referred to as salt A. In a preferred embodiment, the oligodynamic salts comprise one or more salts of oligodynamic metals. The salts may be different salts of the same oligodynamic metal or may be salts of different oligodynamic metals. Oligodynamic metals useful in the present invention include, but are not limited to, silver, platinum, gold, zinc, copper, cerium, gallium, osmium, and the like. The preferred oligodynamic metal is silver.

Salts of other metals may be employed to form the colloid. In the discussion of the process below, these salts are referred to as salt B. These salts contain cationic ions that include, but are not limited to, calcium, sodium, lithium, aluminum, magnesium, potassium, manganese, and the like, and may also include oligodynamic metal cations such as copper, zinc, and the like. These salts contain anions that include, but are not limited to, acetates, acetylsalicylates, ascorbates, benzoates, bitartrates, bromides, carbonates, chlorides, citrates, folates, carbonates, deoxycholates, gluconates, iodates, iodides, lactates, laurates, oxalates, palmitates, para-aminobenzoates, para-aminosalicylates, perborates, phenosulfonates, phosphates, picrates, propionates, salicylates, stearates, succinates, sulfadiazines, sulfates, sulfides, sulfonates, tartrates, thiocyanates, thioglycolates, thiosulfates, and the like, as well as silver proteins and silver ethylenediaminetetraacetic acid. The invention may also be practiced with oxides serving as Salt B, including, but not limited to oxides of calcium, sodium, lithium, aluminum, magnesium, potassium, manganese, and the like, and may also include oligodynamic metal cations such as copper, zinc, and the like.

The compositions can contain auxiliary components. Examples of such auxiliary components include, but are not limited to, viscosity and flow control agents, antioxidants, conventional pigments, air release agents or defoamers, and discolorants. The composition may also contain conventional dyes and pigments to impart color or radiopacity or to enhance the aesthetic appearance of the compositions. The compositions can also contain additional lubricating agents and other additives that enhance patient comfort and tissue health.

While not wishing to be bound by the following mechanism, it is believed that many of the advantageous properties of some embodiments of the present compositions result from the differences in the solubility of the different metal salts present in the colloid. These differing solubilities of the metal salts in the colloid provide varying release kinetics for the active oligodynamic metal(s). For example, with a medical device composed of, or coated with, the compositions of the present invention, those salts that have high water solubility will be released from the coating rather quickly, providing a high initial dose of antimicrobial activity to kill bacteria introduced upon insertion of the device in the patient. This initial dose is sometimes referred to as "quick kill," and this antimicrobial activity is identified by the ability of a coated device or composition to create zones of no bacterial growth around the device or composition when it is placed in a bacterial culture. This test is known as a "zone of inhibition" assay. Those salts having lower water solubilities will be released more slowly from the composition, resulting in a sustained or extended antimicrobial activity over time.

Selection of salts having varying degrees of solubility in the composition allows tailoring of the composition to the specific application of the article comprising the composition. In one embodiment, compositions of the invention are tailored to kill bacteria introduced during the insertion of a medical device, both on the surface of the device and in the surrounding fluid and tissue, by the quick release of antimicrobial metal salts, followed by prolonged inhibition of bacterial migration and growth by the slower release of less soluble antimicrobial metal salts over an extended period of time. In another embodiment, the compositions contain silver salts with a very low solubility, thus reducing the release of silver into the fluid surrounding the article in order to reduce tissue exposure to silver ions while maintaining inhibition of microbial adherence on the surface of the coated article. The ability to tailor the release of the oligodynamic agent is advantageous over conventional antimicrobial compositions, as it provides for both immediate and sustained antimicrobial activity.

The composition may contain any amount of one or more oligodynamic metal salts, oxides, or combination of salts and oxides. In some embodiments, the composition contains between about 40% and about 50% (based on weight of total solids in the composition) of the one or more oligodynamic metal salts, oxides, or combination of salts and oxides. In some embodiments, the composition contains between about 30% and about 40% (based on weight of total solids in the composition) of the one or more oligodynamic metal salts, oxides, or combination of salts and oxides. In some embodiments, the composition contains between about 20% and about 30% (based on weight of total solids in the composition) of the one or more oligodynamic metal salts, oxides, or combination of salts and oxides. In some embodiments, the composition contains between about 15% and about 25% (based on weight of total solids in the composition) of the one or more oligodynamic metal salts, oxides, or combination of salts and oxides. In some embodiments, the composition contains between about 10% and about 20% (based on weight of total solids in the composition) of the one or more oligodynamic metal salts, oxides, or combination of salts and oxides. In some embodiments, the composition contains between about 5% and about 15% (based on weight of total solids in the composition) of the one or more oligodynamic metal salts, oxides, or combination of salts and oxides. In some embodiments, the composition contains between about 3% and about 8% (based on weight of total solids in the composition) of the one or more oligodynamic metal salts, oxides, or combination of salts and oxides. In some embodiments, the composition contains between about 4% and about 6% (based on weight of total solids in the composition) of the one or more oligodynamic metal salts, oxides, or combination of salts and oxides. In some embodiments, the composition contains about 5% (based on weight of total solids in the composition) of the one or more oligodynamic metal salts, oxides, or combination of salts and oxides. In some embodiments, the composition contains greater than zero and up to about 5% (based on weight of total solids in the composition) of the one or more oligodynamic metal salts, oxides, or combination of salts and oxides. In some embodiments, the composition contains greater than zero and up to about 2% (based on weight of total solids in the composition) of the one or more oligodynamic metal salts, oxides, or combination of salts and oxides. In some embodiments, the composition contains between about 3% and about 4% (based on weight of total solids in the composition) of the one or more oligodynamic metal salts, oxides, or combination of salts and oxides. In some embodiments, the composition contains about 2.5% (based on weight of total solids in the composition) of the one or more oligodynamic metal salts, oxides, or combination of salts and oxides. In some embodiments, the composition contains about 1% (based on weight of total solids in the composition) of the one or more oligodynamic metal salts, oxides, or combination of salts and oxides.

In some embodiments, coated articles will reduce adherence of one or more bacteria, fungi, or other microbes to the article as compared to uncoated articles. In one embodiment, the coating results in an in vitro decrease in microbial adherence of 5-95%. In another embodiment, the coating results in a decrease in microbial adherence of at least about 30%. In another embodiment, the coating results in a decrease in microbial adherence of at least about 50%. In another embodiment, the coating results in a decrease in microbial adherence of at least about 75%. In another embodiment, the coating results in a decrease in microbial adherence of at least about 90%. In another embodiment, the coating results in a reduction of at least about 95%. Embodiments exist with any degree of reduction of adherence used. As used herein, reduction of microbial adherence is determined using the procedures set forth in EXAMPLE 18 herein.

In some embodiments, the coated articles have antimicrobial effects upon surrounding tissues and fluids, as can be demonstrated through zone of inhibition testing on one or more species or strains of bacteria, fungi, or other microorganisms. Examples of antimicrobial effects include, but are not limited to, inhibition of growth, killing, and any other deleterious effect on microbes. In other embodiments, no zone of inhibition is created. In still other embodiments, limited zones of inhibition are created. Embodiments also exist in which zones of inhibition are created for some strains in a species but not others, or for some species but not others. Embodiments also exist in which zones of inhibition differ between microbes. As used herein, zones of inhibition is determined using the procedures set forth in EXAMPLE 19 herein. In one desirable embodiment, an article is coated with a composition comprising colloidal silver chloride. The resulting article reduces or eliminates adherence of microbes on the surface of the endotracheal tube but releases silver to surrounding tissues at such a slow rate due to the low solubility of silver chloride that the article does not produce zones in the zone of inhibition assay.

By tailoring the release profile of the oligodynamic metals, it is possible to develop any article having any combination of antimicrobial effects on the surface and surrounding tissues and fluids. Thus, any of the above combinations of effects are achieved. For example, in some embodiments microbial adherence of a specific species or strain of organisms is reduced (including any of the % reductions noted above) while these embodiments produce little or no zone of inhibition for the same species or strain. Embodiments also exist in which both zone of inhibition and microbial adherence differ between organisms.

In some embodiments, the use of the coatings reduces the risk of infection. This action can operate by affecting the surface of the article, affecting surrounding tissues and fluids, or both. For example, use of endotracheal tubes containing a coating of the present invention resulted in reduction of pneumonia occurrence as compared to uncoated tubes. This reduction occurs even though tubes with a similar or the same coating show limited or substantially no zone of inhibition in in vitro testing for the microbes administered to test subjects.

The present invention further comprises methods of treatment and delivery of substances as well as devices in which anywhere from 5-100% of the oligodynamic metals in the compositions are released in the first 24 hours. A variety of release profiles from a single type of article are therefore achieved. In some embodiments, between 75% and 100% of the oligodynamic metal in the coating is released in the first 24 hours. In other embodiments, between 50% and 75% of the oligodynamic metal in the coating is released in the first 24 hours. In other embodiments, between 25% and 50% of the oligodynamic metal in the coating is released in the first 24 hours. In other embodiments, between 0% and 25% of the oligodynamic metal in the coating is released in the first 24 hours. In other embodiments, about 75% of the oligodynamic metal is released in the first 24 hours. In other embodiments, about 75% of the oligodynamic metal is released in the first 24 hours. In other embodiments, about 40% of the oligodynamic metal is released in the first 24 hours. Other embodiments involve releases over a longer period of time. In one embodiment, about 38% is released the first day, and about 80% of the oligodynamic metal is release within 21 days. As used herein, release is determined using the procedures set forth in the elution tests in EXAMPLE 20 herein.

Another advantage of the coating compositions is the wet coefficients of friction (COF) achievable. Coating compositions are manipulated so that highly lubricious coatings are made or hydrophilic coatings with little lubricity are made. Embodiments exist with any achievable COF value. In some medical device embodiments, intermediary COF values ranging between about 0.100 and about 0.0300 are used to reduce the risk of unwanted slippage or movement of a coated article after placement in a location in the body such as a cavity or lumen while providing enough hydrophilicity to reduce tissue irritation and inflammation. In other embodiments where a highly lubricious surface is desired, a COF ranging between about 0.040 and about 0.060 (after one hour immersion in water) is achieved. In some embodiments, a COF ranging between about 0.300 and about 0.400 (after one hour immersion in water is achieved. In other embodiments, a COF ranging between about 0.100 and about 0.200 after one hour immersion is achieved. In other embodiments, a COF ranging between about 0.200 and about 0.300 after one hour immersion is achieved.(0.04-0.06) and a not so lubricious (0.1-0.3) and leave it at that. In another embodiment, a COF ranging between about 0.337 and about 0.373 after one hour immersion is achieved. In other embodiments, a COF ranging between about 0.040 and about 0.060 after one hour immersion is achieved. In other embodiments, a COF ranging between about 0.100 and about 0.300 after one hour immersion is achieved. As used herein, COFs are determined using the procedures set forth in EXAMPLE 21 herein. Although that example deals with endotracheal tubes, it may be used for any coated surface having the same dimensions.

Another advantage of the compositions of the present invention is that the formation of colloids within the polymer composition produces ultra-fine particles that possess a minimal particle size for the metal salts. This minimal particle size retards settling and agglomeration. The use of colloids in the composition also permits incorporation of higher quantities of antimicrobial metal without the difficulties associated with the suspensions used in the prior art.

By reducing or eliminating the problems associated with conventional antimicrobial polymer compositions, the present invention provides reproducible compositions having specific antimicrobial ion concentration with a specific antimicrobial ion release profiles that can be tailored through the specific salt combinations selected to provide optimum antibiotic activity over an extended period of time. For example, compositions of the invention can be tailored to release the bulk of their oligodynamic agents within 5 days for a medical device with a short term use in the body, such as a wound drain, within 14 days for a device such as an endotracheal tube with an intermediary term use, or within 30 days for a device with a longer term use, such as a foley catheter. Longer and shorter terms are possible.

The tailored delivery embodiment of the invention will now be further described in terms of a polyurethane composition containing a colloid of specific silver salts. It is to be understood that this is simply an example of one embodiment of the invention and that one of skill in the art, based upon the present disclosure, can pick and choose salts having differing solubilities to provide a composition having a suitable release profile for a particular purpose.

A coating solution is formed from a 4.7% solution of a polyether polyurethane-urea block copolymer available from CardioTech International, Inc. in a mixture of THF/alcohol in a 75/25 ratio by weight. A sufficient quantity of 10% silver nitrate ($AgNO_3$) solution in water is added to the copolymer solution to produce a final silver concentration of approximately 15%, based on the weight of coating solids in the solution.

Aqueous solutions of sodium chloride, zinc iodide, sodium citrate, sodium acetate, and sodium lactate (each 1.0% solutions) are added to the copolymer solution in sufficient amounts for each salt to react with 15% of the silver nitrate present in the composition. Colloids of silver chloride, silver iodide, silver citrate, silver acetate, and silver lactate are formed in the final coating composition. The coating composition also contains 25% unreacted soluble silver nitrate, as well as the silver nitrate and zinc nitrate salt products. The differences in the solubility of the different salts in the composition will result in different and prolonged rates of release of the oligodynamic silver in the coating composition when a device coated with the composition is exposed to body fluid.

Silver nitrate is the most soluble of the salts present in the composition and will be released rapidly upon initial exposure of the coating to body fluid. Sodium lactate, which has a lower solubility than silver nitrate but a higher solubility than the other salts present, will be released next. Then, the silver acetate, followed by the silver citrate, and then the silver chloride, and, lastly, the silver iodide will be released from the coating composition based upon their relative solubilities.

The initial release and the duration of release of the oligodynamic agents from the composition depends upon several factors. These factors include the relative water solubilities of the particular salts formed in the colloid and the concentration of the salts in the colloid. This release can range, for example, from a few days to several months, and can be tailored through the choice and number of salts formed in the composition for the intended purpose of the device to be coated.

The compositions of the invention can also be tailored to provide other desired properties, such as surface lubricity. Further, the compositions may contain other medicinal or otherwise beneficial agents.

Incorporation of Additional Active Agents into the Copolymer

In some embodiments, the compositions of the present invention contain one or more additional active agents in addition to the oligodynamic metal salts or oxides. The active agents are either retained in the composition or released from the composition at a desired rate or having a desired release profile. Nonlimiting examples of such active agents include antimicrobial agents, such as antibacterial agents, immune boosting agents, anticancer agents, angiogenic agents, polymyxins, antifungal agents, antiviral agents and antibiotics; growth factors, cytokines, immunoglobulins, pharmaceuticals, nutraceuticals, angiostatic agents, including, but not limited to, antithrombogenic agents, antitumoral agents, growth factors, antiangiogenic agents, spermicides, anesthetics, analgesics, vasodilation substances, wound healing agents, plant extracts, and other therapeutic and diagnostic agents. Other active agents useful in the present invention include herbicides, insecticides, algaecides, antifoulants, antifogging agents, and UV and other screening agents. Of these agents, those which can be used for medical applications are preferred. The compositions can also contain salts of metals that enhance the antimicrobial effect of the oligodynamic metal, such as the platinum group metals, or other metals that promote galvanic action. In some embodiments, the combination of additional antimicrobial compounds with oligodynamic metal compounds provide for enhanced antimicrobial activity, for example, by resulting in synergistic antimicrobial activity.

The active agent is advantageously present in the composition in any amount. Desirable amounts include from about 0.1% to about 50% of the dry weight of the composition. Preferred amounts of the active agent are 1% to 30% of the composition based upon the dry weight of the composition.

The following agents have antimicrobial, antibacterial, antiviral, or antifungal activity and are examples of the types of agents that can accompany the polymer and colloid in the composition of the present invention. It will be understood by one of ordinary skill in the art that these are nonlimiting examples and that other active agents can be incorporated into the copolymers of the present invention in a manner similar to the incorporation of the specifically recited agents.

The compositions of the present invention can also contain additional components. For example, the compositions can contain salts of metals that enhance the antimicrobial effect of the oligodynamic metal, such as the platinum group metals, or other metals that promote galvanic action. Further, the composition can include agents that affect the release of the oligodynamic metal.

In some embodiments, the active agent comprises one or more biguanides, many of which have antimicrobial, antiviral, antibacterial, or antifungal activity, or some combination thereof. As used herein, the term "biguanide" includes poly (hexamethylene biguamide) hydrochloride and chlorhexidine compounds. Chlorhexidine is the term denoting the chemical compound N,N"-bis(4-chlorophenyl)-3,12-diimino-2,4,11,13-Tetraazatetradecanediimidamide (CAS registry number 55-56-1). Chlorhexidine compounds include chlorhexidine free base as well as chlorhexidine salts, including but not limited to chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine succinamate, chlorhexidine malate, chlorhexidine tartrate, chlorhexidine dimonoglycolate, chlorhexidine mono-diglycolate, chlorhexidine dilactate, chlorhexidine di-.alpha.-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine isoethionate chlorhexidine di-2-hydroxy-napthoate, and chlorhexidine embonate. Preferred chlorhexidine salts include the acetates, formates, gluconates, hydrochlorides, isoethionates, lactates, and succinamates of chlorhexidine. These biguamide compounds are known in the art and can be prepared by conventional methods. Numerous other biguanides are known and contemplated for use by the present invention. Biguanides can also form polymers. Use of these biguamide polymers is also contemplated by the present invention.

Chlorhexidine is one preferred active agent because it also provides antimicrobial activity. Any effective amount of chlorhexidine can be used. In some embodiments, chlorhexidine is used in an amount greater than zero 0 and up to about 50% based on total solids in the composition by weight. In some embodiments, chlorhexidine is used in an amount greater than 0 and up to about 10% based on total solids in the composition by weight. In some embodiments, chlorhexidine is used in an amount between about 10% and about 50% based on total solids in the composition by weight. In some embodiments, chlorhexidine is used in an amount between about 2 and about 10% based on total solids in the composition by weight. In some embodiments, chlorhexidine is used in an amount between about 10% and about 20% based on total solids in the composition by weight. In some embodiments, chlorhexidine is used in an amount between about 20% and about 30% based on total solids in the composition by weight. In some embodiments, chlorhexidine is used in an amount between about 20% and about 30% based on total solids in the composition by weight. In some embodiments, chlorhexidine is used in an amount between about 25% and about 50% based on total solids in the composition by weight. In some embodiments, chlorhexidine is used in an amount between about 30% and about 40% based on total solids in the composition by weight. In some embodiments, chlorhexidine is used in an amount between about 40% and about 50% based on total solids in the composition by weight.

In some embodiments, the active agent comprises one or more chlorinated phenols, many of which have antimicrobial, antibacterial, antiviral, or antifungal activity, or some combination thereof. Chlorinated phenol compounds which may be used according to the invention include but are not limited to parachlorometaxylenol, dichlorometaxylenol, triclosan (2,4,4'-trichloro-2 hydroxy di-phenyl ether), 2-chlorophenol, 3-chlorophenol, 4-chlorophenol, 2,4-dichlorophenol, 2,4,6-trichlorophenol, 2,3,4,6-tetrachlorophenol, pentachlorophenol, 4-chlororesorcinol, 4,6-dichlororesorcinol, 2,4,6-trichlororesorcinol, alkylchlorophenols (including p-alkyl-o-chlorophenols, o-alkyl-p-chlorophenols, dialkyl-4-chlorophenol, and tri-alkyl-4-chlorophenol), dichloro-m-xylenol, chlorocresol, o-benzyl-p-chlorophenol, 3,4,6-trichlorphenol, 4-chloro-2-phenylphenol, 6-chloro-2-phenylphenol, o-benzyl-p-chlorophenol, and 2,4-dichloro-3,5-diethylphenol. Preferred chlorinated phenols include triclosan and parachlorometaxylenol.

In some embodiments, the active agent comprises one or more quaternary ammonium compounds including but not limited to monomeric and polymeric quaternary ammonium compounds, many of which have antimicrobial, antibacterial, antiviral, or antifungal activity or some combination of the foregoing activities. Examples of quaternary ammonium compounds include, but are not limited to, benzalkonium chloride, benzethonium chloride, other benzalkonium or benzethonium halides, cetylpyridinium chloride, dequalinium chloride, N-myristyl-N-methylmorpholinium methyl sulfate, poly[N-[3-(dimethylammonio)propyl]-N'-[3-(ethyleneoxyethylene dimethylammonio)propyl]urea dichloride], alpha-4-[1-tris(2-hydroxyethyl)ammonium chloride-2-butenyl]-omega-tris(2-hydroxyethyl)ammonium chloride, alpha-4-[1-tris(2-hydroxyethyl)ammonium chloride-2-butenyl]poly[1-dimethyl ammonium chloride-2-butenyl]-omega-tris(2-hydroxyethyl)ammonium chloride, poly [oxyethylene(dimethyliminio)ethylene (dimethyliminio)-ethylene dichloride], ethyl hexadecyl dimethyl ammonium ethyl sulfate, dimethyl ammonium ethyl sulfate, dimethylethylbenzyl ammonium chloride, dimethylbenzyl ammonium chloride, and cetyldimethylethyl ammonium bromide. One preferred quaternary ammonium compound is benzalkonium chloride.

In a further embodiment, the active agent comprises typical antimicrobial agents, growth factors, cytokines, immunoglobulins, or pharmaceuticals and nutraceuticals. Typical active agents that are useful in the present invention as antimicrobial, antiinfective, antiviral, and antibacterial agents include, but are not limited to, alexidine, aminoglycosides (such as gentamicin and Tobramycin), amoxicillin, amphotericin, ampicillin, bacitracin, beclomethasone, benzocaine, benzoic acid, beta-lactams such as pipracil and aztneonam, betamethasone, biaxin, cephalosporins such as ceftazidime, cetrimide, chloramphenicol, clarithromycin, clotrimazole, cyclosporin, docycline, erythromycin, ethylenediamine tetraacetic acid (EDTA), furazolidine, fusidic acid, gramicidin, iodine and iodine complexes such as povidone iodine and pluronic-iodine complex, macrolides, miconazole, minocycline, neomycin, nystatin, octenidine hydrochloride, ofloxacin, parachlorometaxylene, penicillin, pentoxifylline, phenolic compounds (e.g., orthophenylphenol), phenoxymethylpenicillin, picloxydine, polymixin, quinolone antibiotics (such as Norfloxacin, oxolinic acid, ciprofloxacin; Pefloxacin, Enoxacin, AM-833, Pipemidic acid and Piromidic acid, 6,8-difluoro-1-(2-fluoroethyl)-1,4-dihydro-4-oxo-7-(4-methyl-1-piperazinyl)-quinoline-3-carboxylic acid, naladixic acid, and salts thereof) rifampicin, sorbic acid, sulfamylon, sulfonamides, tetracycline, triclocarban, vancomycins, zithromax, derivatives, metabolites, and mixtures thereof, or compounds having similar antimicrobial activity.

Growth factors useful in the present invention include, but are not limited to, transforming growth factor-α ("TGF-α"), transforming growth factor-β ("TGF-β"), vascular epithelial growth factor ("VEGF"), basic fibroblast growth factor, insulin-like growth factor (IGF), vascular endothelial growth factor (VEGF) and mixtures thereof. Cytokines useful in the present invention include, but are not limited to, IL-1, IL-2, IL-3, IL-4, IL-5, IL-6, IL-7, IL-8, IL-9, IL-10, IL-11, IL-12, IL-13, TNF-α, and TNF-β. Immunoglobulins useful in the present invention include, but are not limited to, IgG, IgA, IgM, IgD, IgE, and mixtures thereof.

Some other specific examples of pharmaceutical agents that are useful as active agents include, but are not limited to, nonoxynol 9, acebutolol, acetylcysteine, acetylsalicylic acid, acyclovir, AZT, alprazolam, alfacalcidol, allantoin, allopurinol, ambroxol, amikacin, amiloride, aminoacetic acid, aminodarone, amitriptyline, amlodipine, ascorbic acid, aspartame, astemizole, atenolol, benserazide, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefatroxil, cefazolin, cefixime, cefotaxime, ceftazidime, ceftriaxone, cefuroxime, selegiline, chloramphenicol, chlor-pheniramine, chlortalidone, choline, cilastatin, cimetidine, cisapride, cisplatin, clavulanic acid, clomipramine, clozapine, clonazepam, clonidine, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, estradiol, ethinylestradiol, etoposide, *Eucalyptus globulus*, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, Gingko biloba, glibenclamide, glipizide, *Glycyrrhiza glabra*, grapefruit seed extract, grape seed extract, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexyl, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, N-methylephedrine, naftidrofuryl, naproxen, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, omeprazole, ondansetron, pancreatin, panthenol, pantothenic acid, paracetamol, phenobarbital, derivatives, metabolites, and other such compounds have similar activity. It should be noted that for any term in the foregoing paragraphs that is expressed as a singular term but is sometimes interpreted as describing a class of compounds shall mean any of the group of compounds (e.g. all tetracyclines, all erythromycins, etc.)

Other pharmaceutical agents useful in the present invention include, but are not limited to, other antibacterial, antiviral, antifungal, or antiinfective agents, antithrombogenic agents, anti-inflammatory agents, antitumoral agents, antiangiogenic agents, spermicides, anesthetics, analgesics, vasodilation substances, wound healing agents, other therapeutic and diagnostic agents, and mixtures of these.

In another embodiment, the active agent comprises one or more herbicide, insecticide, algaecide, antifoulant, antifogging agent, or UV or other screening agent.

The compositions of the present invention can contain any combination of these or other active agents. The compositions can also contain additional components such as colorants, discoloration inhibitors, agents that affect the release or rate of release of the active agent, surfactants, adhesion agents, agents that enhance the activity of the active agent, solubilizing agents, agents that enhance the lubricity of the compositions, and other agents which provide beneficial properties to the compositions.

In some embodiments, the compositions contain combinations of two or more of the active agents. Any combination that produces desired results may be used. Some include (along with the polymer and oligodynamic metal colloid): a combination of a biguamide (especially a chlorhexidine compound), a quaternary ammonium compound and a chlorinated phenol (for example, chlorhexidine with benzalkonium chloride and parachlorometaxylenol or triclosan); triclosan and another agent (for example ramicidin, polymixin, norfloxacin, sulfamylon, polyhexamethylene biguamide, alexidine, minocycline, iodine, benzalkonium chloride and rifampicin); chlorhexidine plus triclosan (optionally with silver sulfadiazine either as a part of the colloid or in addition to the colloid); combinations including a chlorhexidine free base and triclosan or a complex resulting from the combination of those two agents. Other examples include silver sulfadiazine (either as a part of the colloid or in addition to the colloid) and sodium piperacillin; silver sulfonamides (either as a part of the colloid or in addition to the colloid) with piperacillin; silver (either as a part of the colloid or in addition to the colloid) with a chlorinated phenol and another antiinfective or antimicrobial agent.

Process for Preparing the Composition

In a second aspect, the present invention relates to a process for producing the compositions of the invention. In general terms, the process comprises the formation of colloids of oligodynamic agents in polymer solutions. The colloid can be formed first and then added to the polymer composition or can be formed in situ in the polymer composition. Preferably, the colloid is formed in situ in the polymer composition.

The process of forming the colloids comprises, for example, combining two or more salts, wherein at least one of the salts is the salt of an oligodynamic agent. These salts will be referred to as salt A and salt B. Salt A comprises one or more oligodynamic agents. Salt B comprises one or more salts that can react with salt A to form a colloid. Salts A and B can be combined in any amount and in any order. In some embodiments, salt A is present in a stoichiometric amount or in excess when compared to salt B. In some embodiments, salt B is present in a stoichiometric amount or in excess when compared to salt A.

Optionally, additional components can be added to the compositions. These components include, but are not limited to, additional oligodynamic agents, additional soluble salts, salts which provide galvanic action, and any other components which provide the compositions with beneficial properties or enhance the antimicrobial activity of the compositions. Such components include, but are not limited to, antimicrobial agents, antibiotics, and other medicinal agents.

In one disclosed embodiment, the composition is produced by forming a solution, dispersion, or combination of solutions and suspensions of one or more polymers. Next, a solution comprising salt A is added to the polymer composition. Then, a solution comprising salt B is added to the polymer composition to precipitate fine colloidal salt(s) of the oligodynamic agent(s) of salt A. Where the oligodynamic agent is a metal salt, the metal cation of salt A reacts with the anion of salt B. Salt B is added to the polymer composition in an amount sufficient to react with some or all of salt A. Optionally, other salts are then added in amounts to react with some or all of the remaining amount of salt A.

In another disclosed embodiment, salt B is added to the polymer composition, followed by the addition of an excess or stoichiometric amount of salt A. In yet another embodiment, salts A and B can be combined to form a colloid which is then added to the polymer composition.

The final polymer composition formed by these processes contains one or more colloidal salts, composed of the oligodynamic cations of salt A and the anions of salt B, and one or more soluble salts, composed of the anions of salt A and the cations of salt B. Additionally, other salts may be added to the composition that do not react in solution but provide some beneficial effect such as stabilization of the colloid, modification of antimicrobial ion release rate, promotion of galvanic action, increase in antimicrobial effectiveness, or enhancement of biocompatibility. Further, other compounds may be added to the composition, including, but not limited to, medicinal agents, lubricants, nutritional agents, antioxidants, dyes and pigments, and other additives.

As noted above, any polymer can be used to form the compositions of the present invention. When hydrophilic polymers are used, it is preferable that the polymers be soluble in water or in organic solvents containing some water. The ability to add water to the polymer composition without precipitating the polymer allows the addition of water-soluble salts directly to the coating composition. The use of water in the polymer composition increases the solubility of the salts, resulting in the formation of finer, more stable colloids. However, it takes longer for the coating compositions to dry when the water content is very high. For this reason, the preferred amount of water in the hydrophilic polymer compositions is about 50% or less. Such concentrations provide for faster drying times while maintaining the beneficial properties provided by the water in the composition.

In contrast, when hydrophobic polymers are used either alone or in combination with hydrophilic polymers, it is desirable to limit the amount of water present in the composition to avoid precipitation of the hydrophobic polymer with the colloid. In such instances the amount of water present in the polymer composition is preferably 1% or less. While it is possible to practice the invention in the absence of water in the composition, it is preferable to have some water present. Thus, when hydrophobic polymers are employed in the present invention, the preferred water content of the polymer compositions is between about 0.1% and 1% by weight. It is advantageous to employ salts that are soluble in alcohols or organic solvents when hydrophobic polymers employed.

Examples of water-soluble silver salts suitable for use in the present invention include, but are not limited to, silver nitrate, silver acetate and silver lactate. Persons skilled in the art will recognize that many of the "Salt B" salts listed above are soluble in water and suitable for use as a water-soluble salt herein. Examples of salts which are soluble in alcohols and organic solvents include, but are not limited to, silver nitrate, sodium iodide, sodium lactate, sodium propionate, sodium salicylate, zinc chloride, zinc acetate, zinc salicylate, gold trichloride, gold tribromide, palladium chloride and hydrogen-hexachloroplatinate. Examples of alcohols that are useful in the present invention include, but are not limited to, methanol, ethanol, propanol, isopropanol, and butanol. Examples of organic solvents that can be used to form solutions of the oligodynamic salts include, but are not limited to, acetone, tetrahydrofuran (THF), dimethylformamide (DMF), dimethylsulfoxide (DMSO), and acetonitrile. These organic solvents are especially useful when they contain a small amount of water.

It is also possible to prepare polymer compositions from supercritical fluids. The most common of these fluids is liquefied carbon dioxide.

In a preferred embodiment, the polymer composition in which the colloid is formed is a hydrophilic polyether polyurethaneurea. This polymer is a substantially noncovalently crosslinked reaction product of one or more diols, water and an organic diisocyanate. The urea segments of the polymer provide improved strength, increased viscoelasticity, and decreased water absorption. These polymers typically absorb water in amounts from 50 to 100% their weight while remaining strong and elastic.

Diols useful in the formation of these polymers include, but are not limited to, medium and long chain poly(oxyethylene) glycols having a number average molecular weights between 250 and 20,000. Example of such diols are "Carbowax" compounds sold by Union Carbide.

Organic diisocyanates useful to form these polymers include, but are not limited to, tetramethylene diisocyanate, hexamethylene diisocyanate, trimethylhexamethylene diisocyanate, dimer acid diisocyanate, isophorone diisocyanate, diethylbenzene diisocyanate, decamethylene 1,10-diisocyanate, cyclohexylene 1,2-diisocyanate, cyclohexylene 1,4-diisocyanate, methylene bis(cyclohexyl-4-isocyanate), 2,4- and 2,6-tolylene diisocyanate, 4,4-diphenylmethane diisocyanate, 1,5-naphthaliene diisocyanate, dianisidine diisocyanate, tolidine diisocyanate, xylylene diisocyanate, and tetrahydronaphthalene-1,5-diisocyanate.

In another preferred embodiment, the polymer coating composition comprises a combination of a hydrophilic polyurethane, a polymer that is similar or identical to the polymer substrate to be coated, and, optionally, other polymers which aid coating adhesion and physical properties. Antimicrobial salt colloids are prepared in this composition as disclosed previously, with the exception that, depending on the second polymer used, some or all of the water used to prepare salt solutions can be replaced with alcohols or other organic solvents to prevent precipitation of the second polymer. Another exception is that the salts elected must be soluble in solvents compatible with those in which the polymers are soluble. As an example of this preferred embodiment, a solution of a hydrophilic polyether polyurethaneurea in THF can be combined with a solution of polyvinyl chloride (PVC) in methylene chloride or THF in equal amounts. Then, silver nitrate can be dissolved in ethanol and added to the solution without precipitation. Ethanol is used to dissolve the silver nitrate instead of water because PVC has a tendency to precipitate when water is added to the solution. Finally, a dilute solution of zinc chloride in ethanol/water can be slowly added to the polymer composition to produce a fine silver chloride colloid without precipitation of the PVC. The final concentration of water in the coating is less than 1%. The coating solution is then used to dip-coat PVC catheters. The finished coating is well adhered, durable, lubricious when wetted, and contains colloidal antimicrobial salts.

In another embodiment, the polymer composition comprises a hydrophilic polymer as defined in application Ser. No. 09/189,240, filed Nov. 10, 1998, herein incorporated by reference. In general, the polymer is a polyurethane-urea-silane copolymer prepared from the following ingredients: (1) one or more polyisocyanate, (2) one or more lubricious polymer having at least two functional groups, which may be the same or different and are reactive with an isocyanate functional group, and (3) one or more organo-functional silanes having at least two functional groups, which may be the same or different and are reactive with an isocyanate functional group and another functional group that is reactive with a silicone rubber substrate. While these copolymers may be prepared in a variety of ways, preferably they may be prepared by first forming a prepolymer from the polyisocyanate(s) and lubricious polymer(s) followed by reaction with the organo-functional silane(s). A catalyst is optionally employed during reaction of the isocyanate with the polyol.

Isocyanates useful to form these polymers include, but are not limited to, 4,4'-diphenylmethane diisocyanate and position isomers thereof, 2,4- and 2,6-toluene diisocyanate (TDI) and position isomers thereof, 3,4-dichlorophenyl diisocyanate, dicyclohexylmethane-4,4'-diisocyanate (HMDI), 4,4'-diphenylmethane diisocyanate (MDI), 1,6-hexamethylene diisocyanate (HDI) and position isomers thereof, isophorone diisocyanate (IPDI), and adducts of diisocyanates, such as the adduct of trimethylolpropane and diphenylmethane diisocyanate or toluene diisocyanate.

Polyols useful to form these polymers include, but are not limited to, polyethylene glycols, polyester polyols, polyether polyols, castor oil polyols, and polyacrylate polyols, including Desmophen A450, Desmophen A365, and Desmophen A160 (available from Mobay Corporation), poly(ethylene adipates), poly(diethyleneglycol adipates), polycaprolactone diols, polycaprolactone-polyadipate copolymer diols, poly(ethylene-terephthalate)diols, polycarbonate diols, polytetramethylene ether glycol, ethylene oxide adducts of polyoxypropylene diols, and ethylene oxide adducts of polyoxypropylene triols.

Catalysts useful to form these polymers include, but are not limited to, tertiary amines, such as N,N-dimethylaminoethanol, N,N-dimethyl-cyclohexamine-bis(2-dimethyl aminoethyl)ether, N-ethylmorpholine, N,N,N',N',N''-pentamethyl-diethylene-triamine, and 1-2(hydroxypropyl) imidazole, and metallic catalysts, such as tin, stannous octoate, dibutyl tin dilaurate, dioctyl tin dilaurate, dibutyl tin mercaptide, ferric acetylacetonate, lead octoate, and dibutyl tin diricinoleate.

Silanes useful to form these polymers include, but are not limited to, N-beta-(aminoethyl)-gamma-aminopropyl-trimethoxy silane and diamino-alkoxysilanes, such as N-(2-aminoethyl)-3-aminopropylmethyl-dimethoxy silane.

These polymers preferably have from 7 to 12% by weight silane based upon the weight of the entire polymer. The preferred ratio of isocyanate functional groups to alcohol or other isocyanate reactive functional groups is from 1.1:1 to 2:1. Viscosity of the polymer solution is a function of molecular weight of the polymer and the solids content of the solution and is controlled by addition of solvent to the solution. The preferred copolymer solution for dip coating has a kinematic viscosity in the range of about 1.5 cS to about 20 cS (centistokes), and a solids content in a range of about 0.4 to about 5.

In yet another embodiment, the polymer composition comprises a solution of a hydrophilic polymer as defined in U.S. Pat. No. 5,290,585, which is hereby incorporated by reference. The polymer is a polyurethane-polyvinyl pyrrolidone prepared by mixing the appropriate amounts of isocyanate, polyol, and polyvinyl pyrrolidone (PVP) stock solution. Additional solvents can be added to adjust the viscosity and solids content. Solids content may be in the range of 0.4 to 15% by weight, depending on the solvent used and other considerations. The stoichiometric ratio of total NCO groups in the isocyanate to total OH groups in the polyol may vary from 0.75 to 3.0. Preferably, the isocyanate has at least two NCO groups per molecule and the polyol has at least two OH groups per molecule. The ratio of polyurethane formed in situ to PVP ranges from 0.05 to 3.0 by weight.

The PVP employed to form these polymers preferably has a mean molecular weight from about 50,000 to 2.5 million Daltons. Specific preferred PVP polymers are Kollidon 90, Luviskol K90, Luviskol K80, and Luviskol K60, all available from BASF Corp. (Parsippany, N.J.) and Plasdone 90, PVP K90, and PVP K120, all available from GAF Corporation.

Isocyanates suitable to form these polymers include, but are not limited to, polymethylenepolyphenyl isocyanate, 4,4'-diphenylmethane diisocyanate and position isomers thereof, 2,4-tolylene diisocyanate and position isomers thereof, 3,4-dichlorophenyl diisocyanate, isophorone isocyanate, and adducts or prepolymers of isocyanates, such as the isocyanate prepolymer available as Vorite 63 from CasChem, Inc. (Bayonne, N.J.). Other examples of polyisocyanates useful in the present invention are those listed in ICI Polyarethanes Book, by George Woods, published by John Wiley and Sons, New York, N.Y. (1987).

Polyols useful to form these polymers include, but are not limited to, polyester polyols, polyether polyols, modified polyether polyols, polyester ether polyols, castor oil polyols, and polyacrylate polyols, including Desmophen A450, Desmophen A365, and Desmophen A160 available from Mobay Corporation (Pittsburgh, Pa.). Preferred polyols include castor oil and castor oil derivatives, such as DB oil, Polycin-12, Polycin 55, and Polycin 99F available from CasChem, Inc. Preferred diols include, but are not limited to, Desmophen 651A-65, Desmophen 1300-75, Desmophen 800, Desmophen-550 DU, Desmophen-1600U, Desmophen-1920D, and Desmophen-1150, available from Mobay Corporation, and Niax E-59 and others available from Union Carbide (Danbury, Conn.).

Suitable solvents for use in the formation of these polymers are those which are capable of dissolving the isocyanate, the polyol, and the polyvinyl pyrrolidone without reacting with any of these components. Preferred solvents include, but are not limited to, methylene chloride, dibromomethane, chloroform, dichloroethane, and dichloroethylene.

When a composition containing this polymeric solution is to be used as a coating, the coating is cured, after application to the substrate, at a temperature in the range of approximately 75° F. to approximately 350° F. for a period in the range of about 2 minutes to about 72 hours.

The process of the invention will now be further described in terms of the formation of a colloid of silver chloride from silver nitrate and sodium chloride in a polyurethane polymer coating solution. It is to be understood that this is simply an example of one preferred embodiment of the invention and that any polymer or combination of polymers and any mixture of salts that will form a colloid within the polymer solution can be employed in the present invention.

First, a 4.7% solution of a polyether polyurethane-urea block copolymer is prepared in a mixture of THF/ethanol in a 75/25 ratio by weight. A sufficient quantity of 10% silver nitrate ($AgNO_3$) solution in water is added to the CardioTech copolymer solution to produce a final silver concentration of approximately 15%, based on coating solids in the solution. An aqueous solution of 1.0% sodium chloride (NaCl) is then slowly added to the solution with stirring in an amount sufficient to react with 50% of the $AgNO_3$. The NaCl reacts with the $AgNO_3$ to produce a colloidal suspension of the poorly water soluble salt, AgCl, and the soluble salt, $NaNO_3$, from half of the $AgNO_3$. The amount of water in the final coating solution is about 30% of the total solvent weight. The final polymer concentration in the coating solution is 3.3%, based upon solvent and polymer weights.

A 16 Fr latex Foley catheter can then be coated with the composition by dipping it into the composition solution, withdrawing it at a controlled rate and drying it using standard methods. The finished coating contains both the water soluble, and therefore fast releasing, $AgNO_3$, and the water insoluble, and therefore slow releasing, AgCl.

Preparation of Compositions Containing an Additional Active Agent

The active agent can be incorporated into the compositions of the present invention by any suitable method. For example, in one embodiment, the active agent is mixed with the components of the copolymer composition in a solvent suitable for both the composition and the active agent. Such solvents include, but are not limited to, those discussed above in the process for making the composition.

In another embodiment, the active agent or agents are mixed with the monomers that form the copolymer prior to polymerization. In this embodiment it is desirable that the active agent will not be deactivated by polymerization conditions and will not interfere with polymerization. The monomeric components are then polymerized by methods known in the art.

In yet another embodiment, the copolymer is formed as described above, followed by addition of the active agent to the copolymer solution.

The active agent may be soluble or insoluble in the polymer compositions of the invention or may be a combination of soluble and insoluble agents. Solubilized active agents may be achieved by any means. In some embodiments, the active agent is first dissolved in a suitable solvent before addition to any of the solutions used to produce the compositions of the invention. In some embodiments, an active agents is solubilized by adding the dry active agent directly to a solution of the compositions of the invention, in which it then dissolves.

Insoluble active agents are used in some embodiments of the invention. In one embodiment, the active agent is dispersed into a separate solvent before addition to the solutions of the invention. In another embodiment, the active agent is dispersed directly into any solution of the used to produce the compositions of the invention. Combinations of these techniques are also used.

Uses of the Composition

In a third aspect, the present invention relates to an article of manufacture. In a preferred embodiment, the antimicrobial composition can be used as a coating on a preformed article to provide antimicrobial activity to the surface of the article and to the environment surrounding the article through the continual release of oligodynamic ions. Any article can be coated with the antimicrobial compositions of the present invention. The composition is particularly suited for the production of medical devices, which include, but are not limited to, catheters (as used throughout this application, the term "catheter" denotes any type of catheter including, but not limited to, urinary catheters, vascular catheters, dialysis catheters, and port catheters), cannulae, stents, guide wires, implant devices, contact lenses, IUDs, peristaltic pump chambers, endotracheal tubes, gastroenteric feeding tubes, arteriovenous shunts, condoms, oxygenator and kidney membranes, gloves, pacemaker leads, and wound dressings.

The coatings can be applied to all or part of any surface or group of surfaces on an article. In some embodiments, one or more entire surfaces of an article are coated. In other embodiments, only part of one or more surfaces is coated. In other embodiments, some surfaces are coated in their entirety while other surfaces are coated only partially. Any combination of surfaces, partial surfaces, or both may be selected for coating or remaining uncoated. Partial coating may be accomplished by, for example, dipping only part of an article into a coating composition or spraying a coating composition on to only a part of the article.

For example, in some embodiments in which underlying articles are transparent while coatings are opaque or translucent, a portion of the article may remain uncoated to allow visual inspection of the inside of those portions of the article, including any lumen therein. In embodiments involving endotracheal tubes, for example, it may be desirable to leave a portion of the tube that will be outside the mouth of the patient uncoated so that it is possible to view the inner lumen of the tube to determine whether a patient is breathing properly.

An example of such an endotracheal tube 10 is shown in FIG. 1. The endotracheal tube comprises an elongate tubular body 12 having an upper end 14 and a lower end 16. A connector 18 is coupled to the body 12 at its upper end 14 for connecting the endotracheal tube to a mechanical ventilator. An inflatable cuff 20 is provided adjacent the lower end 16 of the endotracheal tube 10. The cuff 10 is inflated by means of a valve 30, which is in fluid communication with the cuff 20 by means of an inflation tube 32 and an inflation lumen (not shown) formed in the wall of the tubular body 12. The cuff is inflated in the conventional manner, such as by infusing a air through the valve 30 with a syringe.

The inner and outer surfaces of the endotracheal tube 10 are dipped in a coating solution, such as the one of the compositions described above, which forms an opaque or translucent layer when applied to the tube and permitted to dry. The dipping process coats both the interior and exterior surfaces of the endotracheal tube 10. However, to prevent the entire endotracheal tube from becoming opaque, a portion 40 adjacent the upper end 14 of the tubular body 12 is not coated. The uncoated portion may be provided in any suitable manner, such as by not dipping the upper portion 40 into the coating solution, or by masking the wall of the endotracheal tube adjacent the upper end to prevent the coating composition from coating the upper portion.

The resulting endotracheal tube has an opaque coating applied to substantially the entire endotracheal tube except for the uncoated portion 40 which, when a patient is intubated and the tube is used in its normal manner, resides outside the patient. The physician can thus visualize the presence or absence of moisture or "fogging" through the uncoated walls of the upper portion 40, as an indication of whether the patient is breathing properly.

In the disclosed embodiment of the endotracheal tube 10, the uncoated portion 40 is approximately five centimeters in length. It will be understood, however, that the portion 40 can be shorter or longer, as appropriate, so long as at least a sufficient portion of the tube is coated to provide intended antimicrobial or other effects, and so long as at least a part of the uncoated portion 40 resides outside the patient when the tube is used normally and in its intended manner.

It will also be appreciated that the disclosed practice of leaving a portion of the endotracheal tube uncoated so as to visualize moisture or fogging through the walls of the tube is not limited to the disclosed coatings but includes other coatings, including but not limited to antimicrobial, bactericidal and germicidal coatings, coatings containing active agents of any type, lubricious coatings, and the like, especially coatings which are translucent or opaque when applied to the tube and permitted to dry.

While the embodiment disclosed above contemplates the coating of both the interior and exterior surfaces of the endotracheal tube 10, the invention is equally applicable to coatings which are applied only to the exterior surface or only to the interior surface of the tubular body 12.

In some embodiments, the composition of the invention is prepared as a high solids solution and used alone or mixed with other polymers to form an article rather than a coating on an article. Polymers which are useful to form the articles of the invention include, but are not limited to, natural and synthetic rubber, especially latex rubber, acrylonitrile rubber, PVC plastisol, PVC, polyurethanes, silicone, polycarbonates, acrylates, polyamides, polypropylenes, polyethylenes, polytetrafluoroethylenes, polyvinylacetate, poly(ethylene terephthalate), polyesters, polyamides, polyureas, styrene-block copolymers, polymethyl methacrylate, acrylic-butadiene-styrene copolymers, polystyrene, cellulose, and derivatives and copolymers of any of the above.

As nonlimiting examples, compositions of the invention can be admixed into latex rubber for fabrication of catheters, gloves, and other dipped latex products by standard form dipping methods, and vinyl plastisols can be mixed with compositions of the invention to provide dippable and castable antimicrobial PVC devices. Thus, the final article can be composed of one or more of the compositions of the present invention in admixture with other polymeric components.

Alternatively, compositions of the invention can be formulated into high solids coating compositions that can be used to dip-fabricate a variety of medical devices, such as catheters, stents, gloves, condoms, and the like.

By another method, compositions of the invention can be dried and melt processed, for example, by injection molding and extrusion. Compositions used for this method can be used alone or compounded with any other melt-processable material for molding and extrusion of antimicrobial articles.

When used as a coating, the compositions can be applied by any means, including those methods known in the art. For example, the compositions can be brushed or sprayed onto the article, or the article can be dipped into the composition. For example, the article can be dipped into the antimicrobial polymer solution at a rate of about 10-80 inches per minute (ipm), preferably about 40 ipm. The article is allowed to remain in the antimicrobial polymer solution for a period of about 0-30 seconds, preferably about 5-15 seconds. The article is then withdrawn at a rate of about 10-80 ipm, preferably about 15-30 ipm. Once the article has been coated with the copolymer of the invention, it is allowed to air dry for a period of at least about 10 minutes before drying is completed in an oven for a period of about 5-60 minutes at a temperature in the range of about 40-100° C. Preferably, oven drying occurs for a period of about 15 minutes at a temperature of about 50° C. The coated article can optionally be dried with a hot air stream at a temperature in the range of approximately 40° C. to approximately 100° C. for a period of about 5-60 minutes to remove residual solvent. Persons skilled in the art will understand that the parameters in the foregoing paragraph are merely examples and will vary based on the composition of the substrate and coating and the desired features of the coated objects.

The invention allows manipulation of the amount of oligodynamic metal compounds contained in the article per surface area (expressed in units such as micrograms of oligodynamic metal compound per square centimeter of surface area, or $\mu g/cm^2$). Manipulation of this parameter provides an additional means of controlling release rate or release profile. Any achievable concentration may be used. In some embodiments, the article contains between about 40 and about 50 $\mu g/cm^2$ oligodynamic metal compound or compounds. In some embodiments, the article contains between about 50 and about 100 $\mu g/cm^2$ oligodynamic metal compound or compounds. In some embodiments, the article contains between about 50 and about 75 $\mu g/cm^2$ oligodynamic metal compound or compounds. In some embodiments, the article contains between about 50 and about 60 $\mu g/cm^2$ oligodynamic metal compound or compounds. In some embodiments, the article contains between about 25 and about 50 $\mu g/cm^2$ oligodynamic metal compound or compounds. In some embodiments, the article contains between about 30 and about 40 $\mu g/cm^2$ oligodynamic metal compound or compounds. In some embodiments, the article contains between about 20 and about 30 $\mu g/cm^2$ oligodynamic metal compound or compounds. In some embodiments, the article contains between about 25 and about 30 $\mu g/cm^2$ oligodynamic metal compound or compounds. In some embodiments, the article contains between about 10 and about 20 $\mu g/cm^2$ oligodynamic metal compound or compounds. In some embodiments, the article contains between about 15 and about 20 $\mu g/cm^2$ oligodynamic metal compound or compounds. In some embodiments, the article contains between about 10 and about 15 $\mu g/cm^2$ oligodynamic metal compound or compounds. In some embodiments, the article contains between about 5 and about 15 $\mu g/cm^2$ oligodynamic metal compound or compounds. In some embodiments, the article contains between about 5 and about 10 $\mu g/cm^2$ oligodynamic metal compound or compounds. In some embodiments, the article contains between about 4 and about 7 $\mu g/cm^2$ oligodynamic metal compound or compounds. In some embodiments, the article contains between about 11 and about 14 $\mu g/cm^2$ oligodynamic metal compound or compounds. In some embodiments, the article contains about 13 $\mu g/cm^2$ oligodynamic metal compound or compounds. In some embodiments, the article contains about 8 $\mu g/cm^2$ oligodynamic metal compound or compounds. In some embodiments, the article contains about 8 $\mu g/cm^2$ oligodynamic metal compound or compounds. In some embodiments, the article contains about 28 $\mu g/cm^2$ oligodynamic metal compound or compounds. The foregoing ranges are obtained with coated articles as well as with articles formed from the composition.

Use of the Compositions Containing an Additional Active Agent

As discussed above, in one embodiment, the compositions of the present invention can be coated onto the surface of a substrate or used to form an article. Preferred articles are medical devices. The same is true when the composition comprises one or more active agents.

In one embodiment, an article is first coated with a layer of silver as described, for example in U.S. Pat. Nos. 5,395,651; 5,747,178; and 5,320,908 to Sodervall et al., the disclosures of which are incorporated by reference herein. The composition of the present invention is then coated over the silver coated article in a manner as described above.

In some embodiments, the compositions of the invention comprising the active agent are used in combination with one or more additional coating compositions to coat a surface. Alternatively, the composition is used to form an article to which one or more coatings is thereafter applied. The following is a description of some of the possible coating combinations contemplated by the present invention. This description exemplifies the invention in terms of two layers, a primer or base coat and a top coat. However, the invention encompasses the use of more than two layers, any of which can include the active agents of the present invention. The following combinations of coatings are not intended to be exclusive. One having ordinary skill in the art with the following information would readily recognize additional combinations and be capable of practicing the present invention with such additional combinations. Any combination of coatings may be used.

Some multi-coating embodiments comprise the use of two compositions to provide two distinct coatings on the device or a formed article and a coating. It should be understood that the invention is also practiced with multiples layers following the same principles as described below.

The coatings may contain the same composition or different compositions, so long as one of the coatings comprises the composition of the present invention. Where two or more coating layers are employed in the invention, it is convenient to refer to the coating layer closest to the substrate surface as a primer or base coat and to the coating layer most exterior as the top coat.

The compositions of the present invention can be employed as the base coat, the top coat, or both. They can also be employed as intermediate coating layers when used with other coatings of the present invention or known in the art.

In some embodiments, the substrate base coat comprises a polymeric composition that improves adherence of the other coating layers to the article. In some embodiments, top coats that provide a dry elastic coating that becomes lubricious when wet.

Any of the coating layers can comprise one or more active agents in addition to the colloid. Where multiple coatings contain an active agent, the active agents in the coatings may be the same or different. Further, one or more of the coatings can contain additional agents that provide advantageous properties to the device. For example, any of the coatings, regardless of whether it contains an active agent, can also contain agents that affect the release or rate of release of the active agent. The coatings can also contain agents that improve adhesion of the coatings to the substrate or to the base coat, improve wet lubricity of the surface, inhibit discoloration of the compositions containing active agents that discolor, provide additional therapeutic activity, enhance the activity of the active agent, provide galvanic action for oligodynamic metal, and the like.

Further, the particular polymeric compositions of the coatings can be designed to provide some of the properties listed above, such as improved adhesion, improved lubricity, or to enhance or inhibit release of the active agent.

As with coatings that do not contain active agents, the preferred substrates are medical devices. Such medical devices include, for example, catheters, guidewires, implant devices, contact lenses, IUDs, peristaltic pump chambers, endotracheal tubes, gastroenteric feed tubes, arteriovenous shunts, condoms, and oxygenator and kidney membranes. Use of particular active agents in the various coating layers provides particular beneficial effects. For example, use of antibiotics or antimicrobials, inhibits the adherence of bacteria to the surface of the device and can prevent infection in the surrounding tissue.

Although the compositions of the present invention have many application in connection with medical devices, their use is not limited to such embodiments. In some embodiments, the compositions of the present invention are used to coat consumer products and other surfaces to provide an active agent on the surface. The compositions may be used for any suitable purposes. In some embodiments, the compositions of the present invention are used to coat glass beads, chromatography packing material, and other substances for use as diagnostic agents. An example of such embodiments is use of active agents incorporated in such compositions that can detect the desired chemical or substance to be detected. Detection of the appropriate substance can be performed by conventional methods, such as ELISA assays, radioimmunoassays, NMR, fluorescent spectroscopy, and the like.

While it is preferred to dip coat medical devices, such as catheters and stents, the compositions of the present invention can be coated by any other means including, but not limited to spray or brush coatings.

Other applications for which the copolymer compositions of the present invention are useful include coating the compositions onto surfaces in contact with bodies of water such as the walls of pools or spas, the hulls of boats or ships, and the like to provide algaecidic activity, antifoulant activity, or both. For example, the coatings of the invention can be applied to ship hulls to prevent attachment of invertebrate encrustation (e.g. arthropod or molluscan encrustation), or to pool liners to prevent bioslime.

Other Methods of Use, Including Substance Delivery, and Treatment

Methods of use of compositions of the present invention and articles comprising those compositions also include, but are not limited to, methods of delivering oligodynamic metals, in forms including, but not limited to, ions, salts and oxides of one or more oligodynamic metals or combinations thereof, to a desired location as well as methods of treatment of cells, tissues, and organisms.

In some embodiments in which compositions contain additional active agents, the compositions of the present invention can also be used as delivery agents to deliver one or more active agents to a desired location. The method includes delivery of any active agent or combination of agents, including any of the active agents listed above. In some embodiments, the methods provide delivery of beneficial agents to patients. For such uses, the compositions of the present invention are used, for example, as coatings on substrates, such as medical devices, bandages, or devices known in the art for topical delivery of pharmaceutical agents or to form the articles or parts of such articles.

Some embodiments of methods involve delivery of substances to one or more desired locations. Delivered substances include, but are not limited to, compositions comprising both the polymers and the colloids of oligodynamic compounds, the oligodynamic metal compounds themselves, or oligodynamic metal ions. In embodiments in which the composition contains one or more additional active agents, the delivered substances include such agent or agents. Preferred locations include, but are not limited to, an orifice, tissue, cavity, fluid, or other component of the body of an organism. Other preferred methods include in vitro delivery to tissues, tissue cultures, suspensions of cells, or other substances or preparations. In some embodiments, methods include placing a composition of the present invention in conditions effective to cause delivery of one or more oligodynamic metals or ions, salts or oxides thereof (optionally including additional active agents as well) to the desired location. Examples of such conditions include, but are not limited to an aqueous fluid that will allow diffusion of the oligodynamic metal ions or one or more other active agents from the composition and a location in the body of an organism that will allow diffusion of oligodynamic metal salts or oxides or one or more other active agents into a tissue or a fluid in the body.

Methods of the present invention are useful in treatments of organisms, cells, or tissues. An example of such methods involves placing the polymer composition comprising one or more oligodynamic metal compounds and one or more other active agents, or articles comprising such compositions, under conditions effective to deliver ions or compounds of oligodynamic metals to the target organisms, cells, or tissues. Such compositions may, for example, be implanted, administered, inserted, or otherwise placed in conditions effective to cause the oligodynamic metal salts or ions or one or more other active agents to be delivered to the cells, tissue, organisms, or parts of organisms. Examples of treatments include, but are not limited to, for example, antifungal treatments, antiviral treatments, anti-inflammatory treatments, anesthetic treatments, antiseptic treatments, analgesic treatments, stimulant treatments, depressant treatments, tranquilizer treatments, hormone administration, germicidal treatments, antiprotozoal treatments, antiviral treatments, antineoplastic treatments, antiparasitic treatments, antirheumatic treatments, antibacterial treatments, emetic treatments, antiseptic treatments, treatments for inhibiting restenosis, methods of inhibiting healing, methods of reducing thrombus formation, methods of anticoagulation, methods of reducing encrustation, methods of providing topical protection, methods of deodorization (e.g. of wounds or ulcers), methods of preventing or combating infection, methods of preventing or combating microbial or parasitic infestation, methods of promoting healing, methods of producing a styptic or astringent effect, methods of causing formation of eschars or scars, methods of preventing the formation of eschars or scars, methods of contraception, and methods of treating ulcers, slowly granulating wounds, vaginitis, fistulas, dermatitis, or popodermatitis. Additional examples regarding treatments are disclosed in the discussion of the effects of the composition above, and in the example below.

Any of the terms used in the preceding paragraph to describe effects or treatments are defined to have their broadest possible meanings. Terms that refer to being "anti" a type of target organism or agent (e.g. antimicrobial, antiviral, antibacterial) refers to having any deleterious effects upon those organisms or their ability to cause symptoms in a host or patient. Examples include, but are not limited to, inhibition or prevention of growth or reproduction, killing, and inhibiting any metabolic activity of the target organisms. Terms that refer to being "anti" a type of symptom or condition, or as being a "treatment" for a type of condition or symptom, include but are not limited to any effect that prevents, reduces, cures, accelerates cure or healing, or reduces the severity of one or more conditions or symptoms.

As discussed above, the use of salts and oxides of differing solubilities allows control of release profiles of oligodynamic metals. The methods, compositions, and articles herein may also include other means of controlling release profiles. In some embodiments, articles comprising the compositions are shaped in a specific way to affect release profile. For example, diffusion of oligodynamic metals (and, optionally, one or more other active agents) from polymer compositions comprising the salts is enhanced by fragmenting or pulverizing the polymer compositions. In some embodiments, pulverized compositions are applied to a wound site, ingested, or formed into another shape such as a capsule or a tablet. In other embodiments, release is affected by applying an elevated or reduced temperature, an electric field, a magnetic field, or an electric current to the oligodynamic metal compositions before, during, or after application. Release is also affected by coating compositions and articles with other substances or preparing laminates in which layers have different release profiles or combinations thereof. Layering an object with one or more coatings that dissolve over a given period of time, for example, affords another level of control of release profile. The coatings, envelopes, and protective matrices may be made, for example, from polymeric substances, waxes, oligomeric substances, or combinations thereof. The compositions may also contain additional chemicals that affect the release profile of the oligodynamic metal compounds.

Methods of treatment and methods of delivery of oligodynamic metal salts and oxides (and, optionally, one or more other active agents) can include release from articles containing the compositions including, for example, catheters, cannulae, stents, guide wires, implant devices, contact lenses, IUDs, peristaltic pump chambers, endotracheal tubes, gastroenteric feeding tubes, arteriovenous shunts, condoms, oxygenator and kidney membranes, gloves, pacemaker leads, and wound dressings. The compositions of the present invention may be combined with pharmaceutically or cosmetically acceptable carriers and administered as compositions in vitro or in vivo. Forms of administration include but are not limited to implantation or insertion of a medical device comprising the composition, injections, solutions, lotions, slaves, creams, gels, implants, pumps, ointments, emulsions, suspensions, microspheres, particles, microparticles, nanoparticles, liposomes, pastes, patches, tablets, transdermal delivery devices (such as patches), sprays, aerosols, or other means familiar to one of ordinary skill in the art. Such pharmaceutically or cosmetically acceptable carriers are commonly known to one of ordinary skill in the art. Pharmaceutical formulations of the present invention can be prepared by procedures known in the art using well known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinyl-pyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; dry lubricants (e.g., talc, calcium and magnesium stearate); solid polyethyl glycols; and mixtures thereof.

The terms "pharmaceutically or cosmetically acceptable carrier" or "pharmaceutically or cosmetically acceptable vehicle" are used herein to mean, without limitations, any liquid, solid or semi-solid, including but not limited to water or saline, a gel, cream, salve, solvent, diluent, fluid ointment base, ointment, paste, implant, liposome, micelle, giant micelle, and the like, which is suitable for use in contact with living animal or human tissue, desirably without causing excessive adverse physiological or cosmetic responses, and without excessively interacting with the other components of the composition in a deleterious manner. Other pharmaceutically or cosmetically acceptable carriers or vehicles known to one of skill in the art may be employed to make compositions for delivering the molecules of the present invention.

In some embodiments, formulations are constituted so that they release the active ingredient only or preferably in a particular location, over a period of time, or a combination thereof. Such combinations provide yet a further mechanism for controlling release kinetics.

Methods of in vivo administration of the compositions of the present invention, or of formulations comprising such compositions and other materials such as carriers of the present invention that are particularly suitable for various forms include, but are not limited to, urethral administration, oral administration (e.g. buccal or sublingual administration), anal administration, rectal administration, administration as a suppository, topical application, aerosol application, inhalation, intraperitoneal administration, intravenous administration, transdermal administration, intradermal administration, subdermal administration, intramuscular administration, intrauterine administration, vaginal administration, administration into a body cavity, implantation, surgical administration at the location of a tumor or internal injury, administration into the lumen or parenchyma of an organ, and parenteral administration. Techniques useful in the various forms of administrations above include but are not limited to, topical application, ingestion, inhalation, insertion, surgical administration, injections, sprays, transdermal delivery devices, osmotic pumps, applying directly on a desired site, or other means familiar to one of ordinary skill in the art. Sites of application can be external, such as on the epidermis or into an orifice, or internal, for example a gastric ulcer, a surgical field, or into the lumen of a duct or organ, or elsewhere.

The compositions of the present invention can be applied in the form of creams, gels, solutions, suspensions, liposomes, particles, or other means known to one of skill in the art of formulation and delivery of therapeutic and cosmetic compounds. Ultrafine size particles containing the composition can be used for inhalation delivery. Some examples of appropriate formulations for subcutaneous administration include but are not limited to implants, depot, needles, capsules, and osmotic pumps. Some examples of appropriate formulations for vaginal administration include but are not limited to creams, cervical caps, and rings. Some examples of appropriate formulations for oral administration include but are not limited to: pills, liquids, syrups, and suspensions. Some examples of appropriate formulations for transdermal administration include but are not limited to creams, pastes, patches, sprays, and gels. Formulations suitable for parenteral administration include but are not limited to aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions of the invention are combined with, for example, one or more pharmaceutically or cosmetically acceptable carriers or excipients may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art. The volume of administration will vary depending on the route of administration. For example, intramuscular injections may range in volume from about 0.1 ml to 1.0 ml.

This invention is further illustrated by the following examples, which are not to be construed in any way as imposing limitations upon the scope of the invention.

EXAMPLES

Example 1

To form the coating solution, a 4.7% solution of a polyether polyurethane-urea block copolymer available from CardioTech International, Inc. was prepared in a mixture of THF/alcohol in a 75/25 ratio by weight. A sufficient quantity of 10% silver nitrate ($AgNO_3$) solution in water was added to the CardioTech copolymer solution to produce a final silver concentration of approximately 15%, based on the weight of coating solids in the solution. An aqueous solution of 1.0% sodium chloride (NaCl) was added to the solution in an amount sufficient to react with 50% of the $AgNO_3$ to produce a colloid of the poorly water soluble salt, AgCl, from half of the $AgNO_3$ in the coating solution. The NaCl solution was added slowly to the polymer solution and the solution began to turn cloudy with the formation of the fine colloidal AgCl. The amount of water in the final coating solution was about 30% of the total solvent weight. The final polymer concentration in the coating solution was 3.3%, based upon solvent and polymer weights.

A 16 Fr latex Foley catheter was then coated by dipping it into the coating solution, withdrawing it at a controlled rate to control the thickness of the coating and drying the catheter coating using standard methods. The finished coating contained both the water soluble, and therefore fast releasing, $AgNO_3$ and the water insoluble, and therefore slow releasing, AgCl.

Example 2

The process of Example 1 was repeated, except that a 1.0% solution of zinc chloride was used in place of the 1.0% solution of sodium chloride, resulting in the formation of a silver chloride colloid and zinc nitrate from half the silver nitrate in the coating solution. Zinc chloride was added in an amount of one half the amount of NaCl added in Example 1 because one mole of zinc chloride reacts with 2 moles of silver nitrate.

Example 3

The process of Example 1 was repeated, except that a 1.0% solution of copper chloride was used in place of the 1.0% solution of sodium chloride, resulting in the formation of a silver chloride colloid and copper nitrate from half the silver nitrate in the coating solution. Copper chloride was added in an amount of one half the amount of NaCl added in Example 1 because one mole of copper chloride reacts with 2 moles of silver nitrate.

Example 4

The process of Example 1 was repeated, except that the 1.0% solution of sodium chloride was replaced with a 1.0% solution of sodium iodide, resulting in the formation of a silver iodide colloid and sodium nitrate from half the silver nitrate in the coating solution. Silver iodide is a local antiinfective agent and has a lower water solubility than silver chloride, providing a slower releasing silver salt than silver chloride.

Example 5

The process of Example 1 was repeated, except that the 1.0% solution of sodium chloride was replaced with a 1.0% solution sodium propionate, resulting in the formation of a silver propionate colloid and soluble sodium nitrate, along with the remaining silver nitrate in the solution. Silver propionate is a local antiinfective and is more water soluble than AgCl or AgI, providing a faster releasing salt than silver chloride or silver iodide.

Example 6

The process of Example 1 was repeated, except that the 1.0% solution of sodium chloride was replaced with a 1.0% solution of sodium lactate, resulting the formation of a silver lactate colloid and sodium nitrate, along with the remaining silver nitrate in the coating solution. Silver lactate is a local antiinfective and is more water soluble than sodium propionate, AgCl or AgI, providing one of the fastest releasing silver salts, other than the soluble silver nitrate.

Example 7

The process of Example 1 was repeated, except that the 1.0% solution of sodium chloride was replaced with a solution of sodium acetate, resulting in the formation of a silver acetate colloid and sodium nitrate, along with the remaining silver nitrate in the solution. Silver acetate is a local antiinfective that is more water soluble than sodium propionate, silver chloride, or silver iodide, but less water soluble than silver lactate.

Example 8

The process of each of Examples 1, 2, 3, 4, 5, 6, and 7 was repeated, except that the salt solution was added in an amount sufficient to react with 75% of the $AgNO_3$.

Example 9

The process of each of Examples 1, 2, 3, 4, 5, 6, and 7 was repeated, except that the salt solution was added in an amount sufficient to react with 100% of the $AgNO_3$.

Example 10

The process of each of Examples 1, 2, 3, 4, 5, 6, and 7 was repeated, except that the salt solution was added in an amount sufficient to react with 25% of the $AgNO_3$.

Example 11

The process of Example 1 was repeated, except that the NaCl salt solution was added in an amount sufficient to react with 25% of the silver nitrate. Then a 1.0% solution of sodium iodide was added in an amount sufficient to react with another 25% of the silver nitrate to produce a combination of silver chloride and silver iodide colloids from 50% of the silver nitrate.

Example 12

The process of Example 1 was repeated, except that the NaCl salt solution was added in an amount sufficient to react with 25% of the silver nitrate to produce the poorly soluble silver chloride colloid. Then a 1.0% solution of sodium propionate was added in an amount sufficient to react with another 25% of the silver nitrate to produce the slightly water soluble silver propionate colloid. Next, a 1.0% solution of sodium acetate was added in an amount sufficient to react with another 25% of the silver nitrate to produce the somewhat water soluble silver acetate colloid in combination with the poorly soluble silver chloride colloid and the slightly soluble silver propionate colloid from 75% of the silver nitrate.

Example 13

The process of Example 12 was repeated, except that an additional amount of zinc iodide was added to convert 10% of the remaining silver nitrate to a colloid of silver iodide. This produced a coating containing 15% silver nitrate, 25% of the somewhat soluble silver acetate colloid, 25% of the slightly soluble sodium propionate colloid, 25% of the poorly soluble silver chloride colloid, and 10% of the very poorly soluble silver iodide colloid, along with the soluble sodium nitrate and zinc nitrate salt products.

As shown by the above examples, any combination of additional salts in any combination of different amounts can be used to convert some or all of the soluble oligodynamic metal salts into insoluble colloidal salts within a polymer composition.

Example 14

Somewhat water soluble silver salts, such as silver lactate or silver acetate, can be used alone or in combination with the very soluble silver nitrate to produce other compounds that can have antiseptic activity. For example, silver acetate at a 4:1 molar ratio with zinc chloride produces 50% silver chloride colloid and the zinc acetate counter salt, which is also an antiseptic, and leaves 50% unreactive silver acetate. Similarly, other silver salts can be used alone or in combination to produce multiple counter salts that have antiseptic or other desirable activity.

For example, the process of Example 2 was repeated except that a soluble combination of silver nitrate, silver acetate, and silver lactate was used in place of the 10% silver nitrate solution. When the zinc chloride is added, a colloid of silver chloride is formed in the polymer composition and the soluble counter salts zinc nitrate, zinc acetate, and zinc lactate are produced. The zinc acetate and zinc lactate provide antiseptic activity in addition to the antimicrobial activity of the silver salts. In this example any metal salt other than zinc chloride which produces counter salts with the nitrate, acetate, and lactate that have a desired effect, such as antiseptic or antimicrobial activity, can be used. An example of such a salt is copper chloride.

Different oligodynamic salts have different water solubilities. This allows for tailoring of the composition to provide a specific release profile of the antimicrobial agent(s) from the composition. For example, sodium chloride, zinc iodide, sodium citrate, sodium acetate, and sodium lactate can be added to a coating composition containing silver nitrate to produce a coating which contains the water soluble salts silver nitrate and zinc nitrate, the somewhat water soluble salts silver lactate (67 mg/ml water) and silver acetate (10 mg/ml water), the slightly soluble salt silver citrate (0.3 mg/ml water), the poorly soluble salt silver chloride (0.002 mg/ml water), and the very poorly soluble salt silver iodide (0.00003 mg/ml water). By adjusting the proportions of salts having different solubilities in the composition, the release rate of the active oligodynamic agent(s) can be altered to provide a shorter or longer release profile over time.

For example, the process of Example 1 was repeated, except that in addition to the NaCl salt solution, 1% solutions of zinc iodide, sodium citrate, sodium acetate and sodium lactate were added, each in an amount sufficient to react with 15% of the silver nitrate, to produce colloids of silver chloride, silver iodide, silver citrate, silver acetate, and silver lactate in the final coating composition, along with 25% unreacted silver nitrate, and the silver nitrate and zinc nitrate salt products. The difference in solubility of the different silver salts will produce different and prolonged rates of silver ion release in the coating when exposed to body fluid.

Example 15

To form the coating composition for PVC catheters, a 3.3% solution of a polyether polyurethane-urea block copolymer available from CardioTech International, Inc. was prepared in THF. A 3.3% solution of Polyvinyl chloride (PVC) was then prepared in methylene chloride. The two solutions were then combined in equal amounts to provide a 50/50 ratio by weight of the two polymers in solution. A sufficient quantity of 10% silver nitrate ($AgNO_3$) solution in alcohol was then added to the polyurethane-urea/PVC polymer solution to produce a final silver concentration of approximately 5%, based on coating solids in the solution. A 1% zinc chloride solution in a 75/25 mixture by weight of ethanol/water was added to the coating solution in an amount sufficient to react with 50% of the $AgNO_3$ to produce a colloid of the poorly water soluble salt AgCl from half of the $AgNO_3$. The $ZnCl_2$ solution was added slowly to the polymer solution with stirring, and the solution began to turn cloudy with the formation of the fine colloidal AgCl. The amount of water in the final coating solution was slightly less than about 1% of the total solvent weight. A PVC endotracheal tube was then coated by dipping it into the coating composition, followed by drying using standard methods. The finished coating contained both the water soluble, and therefore fast releasing, $AgNO_3$ and the poorly water soluble, and therefore slow releasing, AgCl.

Example 16

Dog Intubation Study

Twelve adult mongrel dogs were orally intubated. Dogs were randomly assigned to be orally intubated either with an endotracheal tube with a coating of the present invention or a noncoated endotracheal tube. The animal care providers were blinded to the animals' study group assignments and all interpretation of the microbiology data and histology data were performed by blinded observers. The animals were assigned to their study groups using a random-number generator. Cuffed endotracheal tubes (Intermediate Hi-Lo, 7.5 mm internal diameter, Mallinckrodt Medical, St. Louis, Mo.) were used for the control animals. For the test animals, the inner and outer surfaces of identical endotracheal tubes were coated with a coating of the present invention.

The test coating was composed of a polymer blend that was 50% polyvinyl chloride (PVC) and 50% polyurethane. The coating had a silver content on the device surface of 3.3 micrograms/$cm^2$. The silver was a colloid of silver chloride that had been prepared by combining sodium chloride with silver nitrate in a polymer solution. The tubes for the control and test groups were repackaged and sterilized with ethylene oxide.

Twelve mongrel adult dogs (17 to 31 kg; Levon Thalen; Strathmore, A B, Canada) were used in the study. Six animals were assigned to receive the coated endotracheal tubes, while six animals received standard noncoated endotracheal tubes. All animals were healthy and free of disease prior to the initiation of the study. Animals that had received any antibiotics <1 week prior to the study were excluded.

The animals were anesthetized with a single injection of sodium pentobarbital (30 mg/kg) and were maintained in a state of anesthesia by providing sodium pentobarbital at approximately 1 mg/kg/h. They were placed in the dorsal recumbent position for the duration of the mechanical ventilation proposed in the study protocol (i.e., up to 4 days of mechanical ventilation). Animals were provided lactated Ringers solution at a rate of 100 mL/h, and urinary catheters were placed to provide urinary drainage. Following tracheal intubation, animals were placed on a ventilator (Harvard Biosciences; South Natick, Mass.) set to deliver 350 to 500 mL tidal volume of room air (50% relative humidity) at a rate of 15 to 20 breaths/min. The tidal volume delivered to the animals was selected and maintained to provide peak airway pressures of <30 cm $H_2O$ throughout the duration of mechanical ventilation. All animals received a level of positive end expiratory pressure of 5 cm $H_2O$.

Prior to the bacterial challenge, blood and buccal culture samples were taken from each animal. After sedation and tracheal intubation, each animal was challenged twice (at 1 and 8 hours (h) after the tracheal intubation) with a respiratory isolate of *Pseudomonas aeruginosa* (strain PAO1). For each challenge, 5 mL of approximately $10^7$ cfu/mL of a log-phase culture of *P. aeruginosa* was instilled into the buccal pouch of the animals. The animals were positioned with their heads turned so that any excess fluid drained out from the mouth, rather than down into the pharynx.

Buccal culture samples were taken every 24 hours after intubation and were plated quantitatively on both nutrient agar and *P. aeruginosa* isolation agar to identify the total amount of aerobic bacteria and the challenge bacteria. Using sterile suctioning tubes and mucous specimen traps, animals were suctioned via the inner lumen of their endotracheal tubes three times per day to remove secretions. However, a minimal amount of recovered tracheal aspirate hindered any attempt to quantitatively assess the bacterial burden from these samples. Rather, the presence of bacteria within the endotracheal tubes was assessed by daily sampling of the endotracheal tube lumens with a cotton culture swab.

Body temperature was monitored continuously and was recorded three times daily to determine the presence of fever in the animals. Blood samples were taken daily from each animal and were cultured using an automated blood culture system (Bactec NR860; Becton-Dickinson; Franklin Lakes, N.J.). The bacteria were identified as *P. aeruginosa*, other pathogenic aerobic bacteria, or contaminants, using standard microbiological methods.

Animals were sacrificed by an overdose of sodium pentobarbital after receiving 96 hours of mechanical ventilation. Postmortem examinations were conducted within 4 to 6 hours of death for all animals using criteria that were determined prospectively in the study protocol. Any indwelling devices (e.g., IV catheter or urinary catheter) were cultured. Gross postmortem examinations were conducted on each dog. The endotracheal tube was removed by dissection, rather than by being pulled out, to prevent the removal of adherent bacteria and secretions. The lungs and the trachea were removed from each animal and weighed.

The gross lung appearance was recorded and scored according to the following scheme: 0, normal; 1, hyperemia, edema, and congestion involving <10% of examined lungs; 2, hyperemia, edema, and congestion involving 10 to 29% of the lungs; 3, hyperemia, edema, and congestion involving 30 to 60% of the lungs; and 4, hyperemia, edema, and congestion involving >60% of the lungs.

The gross appearance of the endotracheal tube also was assessed using the following scheme: 0, no mucus or purulent material on the surface of the endotracheal tube; 1, mucus covering <10% of the endotracheal tube length and <10% obstruction of the endotracheal tube lumen; 2, mucus or purulent material covering or obstructing 10 to 25% of the endotracheal tube surface and/or lumen; 3, mucus covering or obstructing 25 to 50% of the endotracheal tube surface and/or lumen; and 4, mucus covering or obstructing >50% of the surface and/or lumen of the endotracheal tube.

Tissue samples from each identified primary lung lobe were collected for quantitative cultures (i.e., total bacteria and *P. aeruginosa*) and histologic examination. As all animals were placed in the dorsal recumbent position, the diaphragmatic lobes (caudal lobes) were determined to be in a dependent position. Additionally, samples from the mid-portions of the two mainstem bronchi and the trachea (i.e., proximal trachea [i.e., upper third of the trachea], middle trachea [i.e., just above the cuff of the endotracheal tube], and distal trachea [i.e., tracheal surface in contact with the cuff of the endotracheal tube]) were collected for quantitative microbiology.

Cultures from the inner lumen surface of the endotracheal tube were collected at the postmortem examination from three 1-cm segments of the tube. The three samples were taken from the proximal third of the endotracheal tube, from the portion of the tube just proximal to the cuff, and from the cuffed portion of the endotracheal tube. The inner lumen surface from the cut pieces of the endotracheal tubes were swabbed with cotton-tipped applicators to identify the bacteria. The applicators then were sonicated and plated onto the appropriate medium to enumerate the amount of total bacteria as well as that of *P. aeruginosa*.

Microbiology

For each tested tissue sample, a weighed, aseptically prepared tissue portion was homogenized in sterile phosphate-buffered saline solution (5 mL). This was serially diluted, and 100 µl was spread-plated onto nutrient agar and *P. aeruginosa* isolation agar to obtain quantitative cultures using techniques described in: Baselski V S, et al. "The standardization of criteria for processing and interpreting laboratory specimens in patients with suspected ventilator-associated pneumonia." *Chest* 1992; 102[suppl]:571S-579S.

Histologic Interpretation

All microscopic samples were scored based on the grading scale described below by an animal pathologist (MEO) and were scored independently by a second animal pathologist (BGH). Both pathologists were blinded to the experimental protocol and the region of sampling. The histologic classification of lung tissue specimens was similar to that employed by other investigators (Baron et al. "Classification and identification of bacteria." In: Murray P R, ed. *Manual of clinical microbiology*. Washington, D.C.: ASM Press, 1995; 249-264; Marquette, et al. "Characterization of an animal model of ventilator-acquired pneumonia." *Chest* 1999; 115:200-209). Fresh tissue samples were fixed in 10% neutral buffered formalin. After fixation for >24 h, samples were dehydrated in ethanol and xylene and were embedded in paraffin. After sectioning, tissue samples were stained with hematoxylin-eosin. Sections were examined and photographed on a light microscope (Nikon; Tokyo, Japan), after which each photograph was assigned a unique and permanent identification number.

Histology samples of the lung were scored using several scales.

Hyperemia: 0, no hyperemia; 1, (slight) capillaries distended with blood; 2, (moderate) capillaries distended with blood and some alveoli filled with serous fluid and/or blood; and 3, (severe) capillaries are distended with blood and most alveoli are filled with serous fluid and/or blood.

Edema: 0, no edema; 1, slight interstitial fluid accumulation; 2, serous fluid in alveoli and moderate interstitial fluid accumulation; and 3, large amounts of serous fluid in alveoli and excessive interstitial fluid accumulation.

Cellular infiltration: 0, no cellular infiltration into alveolar or interstitial space; 1, occasional neutrophils; lymphocytes and/or large mononuclear cells in the alveoli and interstitial space associated with some alveoli; 2, moderate numbers of neutrophils, lymphocytes, and large mononuclear cells in the alveoli and interstitial space associated with most alveoli; and 3, large numbers of neutrophils, lymphocytes, and large mononuclear cells in the alveoli and interstitial space of most alveoli.

Bacteria: 0, no bacteria visible; 1, occasional bacteria evident within phagocyte; 2, bacteria within most phagocytes and occasional free bacteria; and 3, large numbers of bacteria present within phagocytes and within the alveolar and interstitial spaces.

Data were reported as the mean±SD. All primary comparisons between the test and control animals were based on the data for each lobe, unless otherwise noted. The Fisher's Exact Test was used to compare categoric data, and the Mann-Whitney test was used to compare non-normal, continuous data. The Spearman rank test was used to correlate histologic and microbiology data for each lobe. The κ statistic was used to assess the interobserver agreement for lung infiltration with neutrophils.

Intubation was performed without difficulty and was achieved on the first attempt for all animals. Six of the animals that had received noncoated endotracheal tubes and five that had received silver-coated tubes completed the study protocol and were included in the data analysis. One animal receiving a silver-coated endotracheal tube died 6 h after intubation. This animal mistakenly received an initial tidal volume of >500 mL, resulting in pneumothorax and subsequent death by an overdose of sodium pentobarbital. The lungs appeared normal at necropsy, and this animal was not included in the data analysis as it did not receive the bacterial challenge with *P. aeruginosa*. There was no statistical difference in the duration of mechanical ventilation and the day of death for dogs receiving either the noncoated or the silver-coated endotracheal tubes (3.0±1.5 vs. 3.6±0.5 days, respectively; p=0.330). Three of five animals (60.0%) that had been treated with silver-coated endotracheal tubes survived to the end of the study period at 96 h compared to three of the six control animals (50.0%; p>0.999). The cause of death for the dogs receiving silver-coated endotracheal tubes included euthanasia for the three dogs completing the protocol, and cardiac arrest and renal failure for the two dogs not completing the study protocol, which were expected complications among mechanically ventilated dogs. The cause of death for the dogs receiving noncoated endotracheal tubes included euthanasia for the three dogs completing the protocol, septic shock from *P. aeruginosa* bacteremia in two animals, and excessive purulent secretions resulting in endotracheal tube occlusion in one animal.

Buccal Cultures: For both test and control dogs, the concentration of *P. aeruginosa* in the buccal secretions increased within 24 h after anesthesia administration and inoculation to >$10^8$ cfu/g aspirate. No statistical differences were seen between the two groups for the degree of buccal colonization throughout the duration of the study period.

Figure 2:
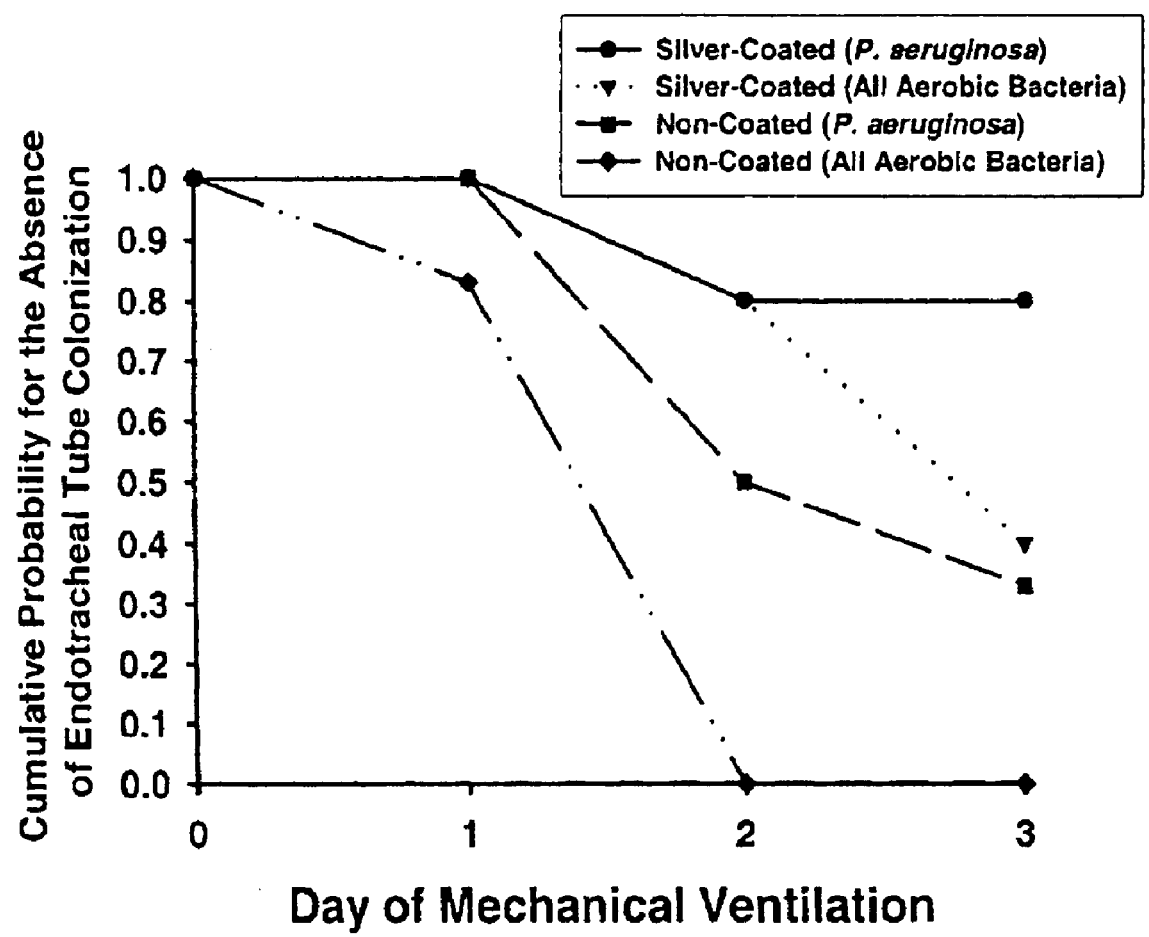
FIG. 2 shows the cumulative probability of the absence of endotracheal tube colonization with *P. aeruginosa* and aerobic bacteria among dogs receiving endotracheal tubes coated with a coating of the present invention and that among dogs receiving uncoated tubes. The tubes were involved in the dog intubation study in Example 16 herein.

Endotracheal Tube Lumen Cultures: The average time until colonization with *P. aeruginosa* of the inner lumens of the noncoated and silver-coated endotracheal tubes was 1.8±0.4 and 3.2±0.8 days, respectively (p=0.016). On day 2 of mechanical ventilation, the inner lumens of six of six (100.0%) noncoated endotracheal tubes were colonized by aerobic bacteria and 1 of 5 (20.0%) silver-coated endotracheal tubes were colonized with aerobic bacteria (p=0.015). Three of six noncoated endotracheal tubes (50.0%) and one of five silver-coated endotracheal tubes (20.0%) were colonized with *P. aeruginosa* on day 2 of mechanical ventilation (p=0.546). FIG. 2 shows the cumulative probability of the endotracheal tubes having cultures negative for *P. aeruginosa* or aerobic bacteria for the 3 days following intubation and inoculation of the dogs.

The concentration of aerobic bacteria from the sampled inner lumen segments of the endotracheal tubes at the time of necropsy was greater than that for the noncoated endotracheal tubes compared to the silver-coated endotracheal tubes (6.1±1.3 vs. 4.1±2.1 log cfu/cm, respectively; p=0.009). Similarly, the concentration of *P. aeruginosa* from the sampled inner lumen segments of the endotracheal tubes was greater for the noncoated endotracheal tubes (4.1±1.0 vs. 2.6±1.9 log cfu/cm, respectively; p=0.076).

Tracheal and Bronchial Cultures: The trachea and mainstem bronchi were heavily colonized with *P. aeruginosa* at postmortem examination. The upper, mid-portion, and distal trachea, and the mainstem bronchi were more heavily colonized with *P. aeruginosa*, and all aerobic bacteria, among dogs receiving noncoated endotracheal tubes compared to dogs receiving silver-coated endotracheal tubes (Table 1). However, these differences did not reach statistical significance.

receiving silver-coated endotracheal tubes. *P aeruginosa* bacteremia was seen in two of six control animals and in zero of five test animals. *Staphylococcus aureus* was isolated from the blood of one dog receiving a noncoated endotracheal tubes and in one dog receiving a silver-coated endotracheal tube. For the three control animals, the positive blood cultures were found on days 2, 3, and 4. The positive blood culture was seen in the test animal on day 4.

Postmortem Examination

Endotracheal Tubes Gross Appearance: Five of six of the noncoated endotracheal tubes (83.3%) and zero of five of the silver-coated endotracheal tubes (0.0%) had at least a 50.0% narrowing of their lumens due to the presence of mucus at necropsy (p=0.015). The mean gross appearance score for the noncoated endotracheal tubes was statistically greater than for the silver-coated endotracheal tubes (3.6±1.2 vs. 1.2±0.8, respectively; p=0.030).

Lungs: There was no statistical difference in the mean weight of the lungs for the animals receiving the noncoated and silver-coated endotracheal tubes (634±130 vs. 592±53 g, respectively; p=0.524). The mean scores for the gross

TABLE 1

Bacterial Counts in the Trachea and Mainstem Bronchi*

| | *P aeruginosa* | | | All Aerobic Bacteria | | |
| --- | --- | --- | --- | --- | --- | --- |
| Location | Dogs receiving Noncoated Endotracheal Tubes (n = 6) | Dogs receiving Silver-Coated Endotracheal Tubes (n = 5) | p Value | Dogs receiving Noncoated Endotracheal Tubes (n = 6) | Dogs receiving Silver-Coated Endotracheal Tubes (n = 5) | P Value |
| Proximal trachea | 6.2 ± 0.8 | 5.5 ± 0.7 | 0.234 | 6.9 ± 0.6 | 6.1 ± 0.5 | 0.083 |
| Mid-trachea | 5.8 ± 0.6 | 5.3 ± 0.7 | 0.272 | 7.1 ± 0.9 | 6.4 ± 0.8 | 0.315 |
| Distal trachea | 5.8 ± 0.7 | 4.8 ± 0.8 | 0.054 | 6.7 ± 0.8 | 6.3 ± 1.2 | 0.647 |
| Mainstem bronchi | 4.4 ± 2.4 | 3.6 ± 2.0 | 0.111 | 5.6 ± 1.0 | 4.5 ± 1.0 | 0.054 |

*Values given as mean log cfu/g (±SD), unless otherwise indicated.

Figure 3:
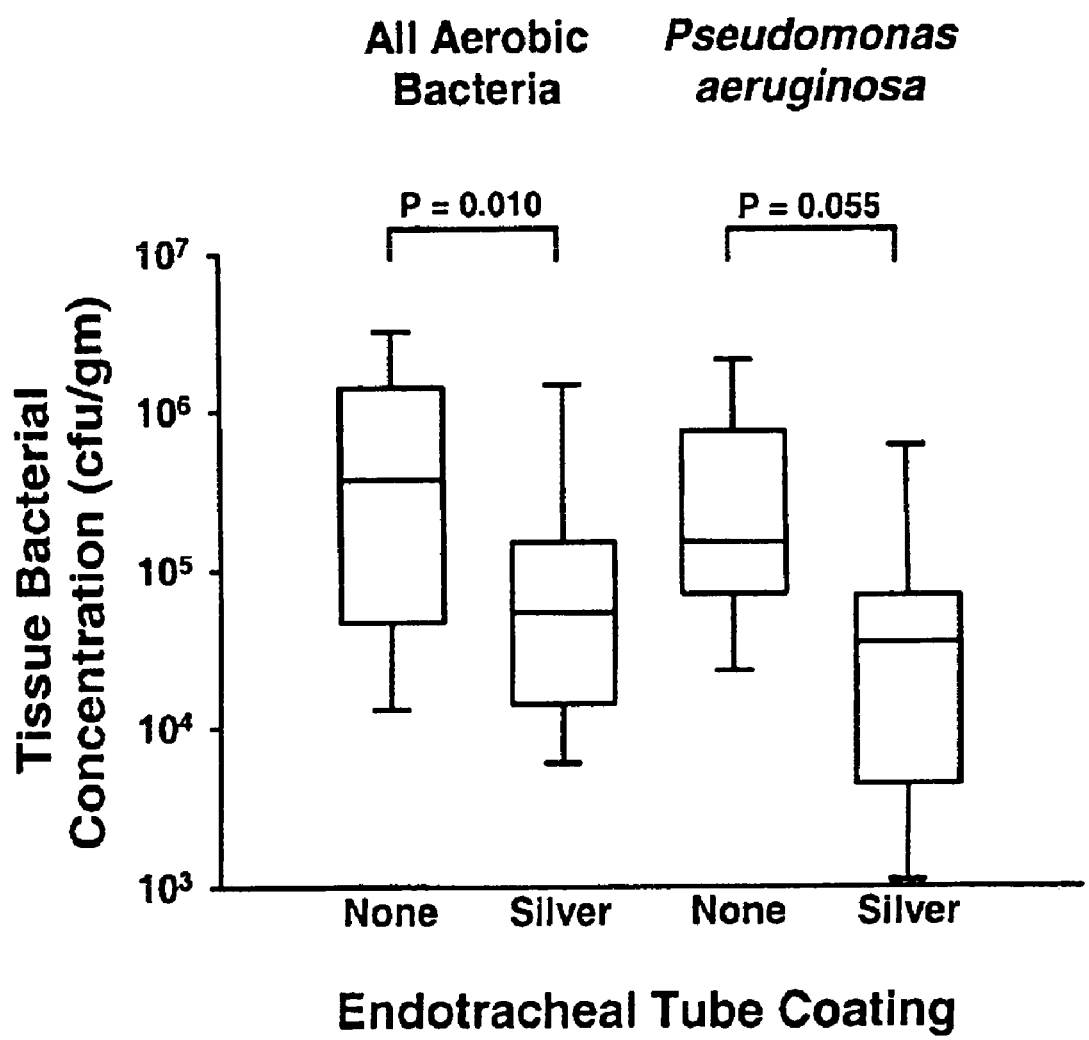
FIG. 3 shows box plots of tissue bacterial concentrations for all aerobic bacteria and *P. aeruginosa* for endotracheal tubes having a coating of the present invention and for uncoated tubes. The tubes were involved in the dog intubation study in Example 16 herein. Boxes represent $25^{th}$ to $75^{th}$ percentiles with the $50^{th}$ percentile (solid line) shown within the boxes. The $10^{th}$ and $90^{th}$ percentiles are shown as capped bars.

Lung Parenchymal Cultures: Bacteria were cultured from all lung tissue samples that were taken at necropsy. The total aerobic bacterial burden in the lung parenchyma was statistically lower among the dogs that had received the silver-coated endotracheal tubes (4.8±0.8 vs. 5.4±0.9 log cfu/g lung tissue, respectively; p=0.010) (Shown in FIG. 3). The tissue concentration of *P. aeruginosa* among dogs in the silver-coated group was also lower compared to dogs in the noncoated endotracheal tube group (4.3±1.2 vs. 4.4±2.1 log cfu/g lung tissue, respectively; p=0.055). The achieved thresholds of *P. aeruginosa* among the 36 lung lobes from dogs receiving noncoated endotracheal tubes were 29 (80.6%) with $\geq 10^4$ cfu/g, 19 (52.8%) with $\geq 10^5$ cfu/g, and 6 (16.7%) with $\geq 10^6$ cfU/g, compared to 20 (66.7%) with $\geq 10^4$ cfu/g, 7 (23.3%) with $\geq 10^5$ cfu/g, and 3 (10.0%) with $\geq 10^6$ cfu/g among the 30 lung lobes from dogs receiving silver-coated endotracheal tubes (p=0.105). The achieved aerobic bacterial thresholds among the 36 lung lobes from dogs receiving noncoated endotracheal tubes were 34 (94.4%) with $10^4$ cfu/g, 24 (66.7%) with $\geq 10^5$ cfu/g, and 13 (36.1%) with $\geq 10^6$ cfu/g, compared to 25 (83.3%) with $10^4$ cfu/g, 9 (30.0%) with $\geq 10^5$ cfu/g, and 4 (13.3%) with $\geq 10^6$ cfu/g among the 30 lobes from dogs receiving silver-coated endotracheal tubes (p=0.028).

Figure 4:
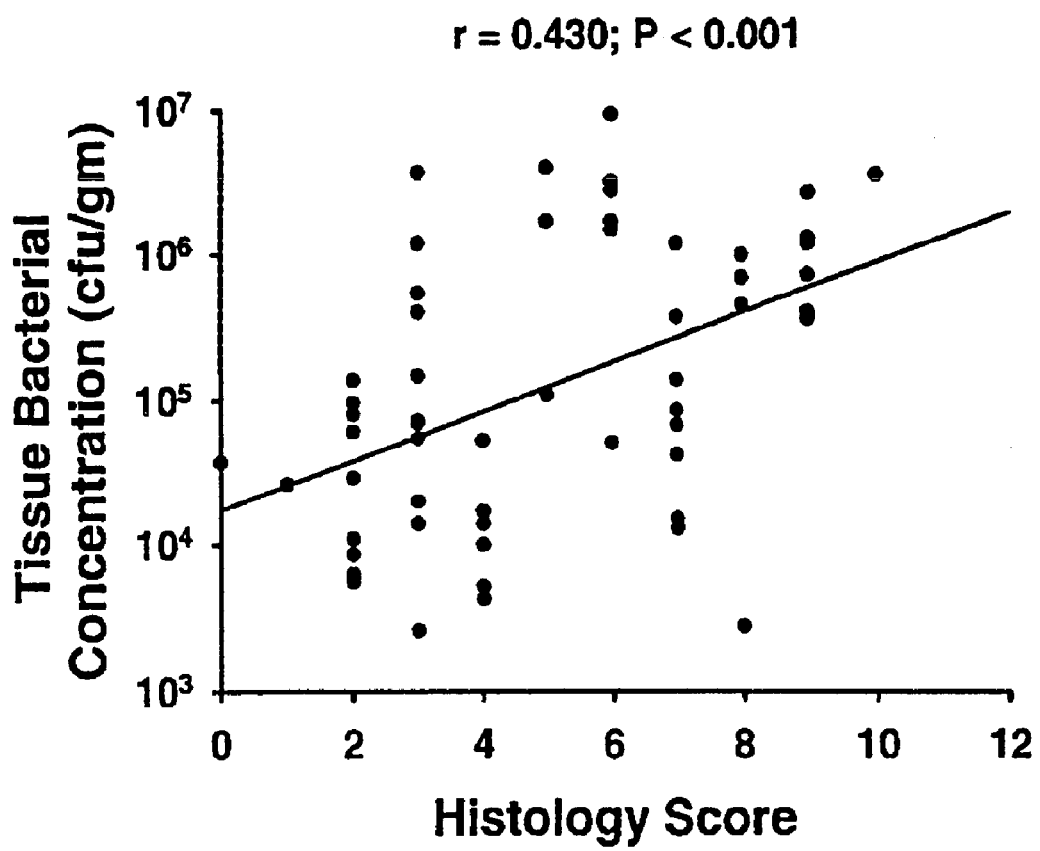
FIG. 4 is a scatter plot of histology scores (x-axis) plotted against the lung tissue concentration of total aerobic bacteria (y-axis). The plotted data was generated by the dog intubation study in Example 16 herein. The regression line is shown.

Blood Cultures: Bacteria blood cultures were seen in three of six (50.0%) control animals and in one of the five animals appearance of the entire lung for the dogs receiving noncoated and silver-coated endotracheal tubes were 3.2±1.2 and 1.2±0.4, respectively (p=0.030). The major pathologic findings were congestion and hyperemia in both groups. Both veterinary pathologists found statistically significant differences in the histologic evaluation of the dogs receiving noncoated endotracheal tubes compared to the dogs receiving silver coated endotracheal tubes (MEO: 7.1±1.6 vs. 2.8±1.2, respectively [p<0.001]; BGH: 3.0±0.7 vs. 2.1±1.3, respectively [p=0.001]). FIG. 4 depicts a scatter plot of histology scores (x-axis) plotted against the lung tissue concentration of total aerobic bacteria (y-axis). The regression line is also shown.

The most prominent histologic changes consisted of diffuse neutrophil infiltration into the alveolar walls and capillaries, which was noted primarily in the dogs receiving noncoated endotracheal tubes. One observer (BGH) noted that 21 of 33 lung lobes (63.6%) from dogs receiving noncoated endotracheal had large numbers of interstitial neutrophils present compared to only 1 of 28 lung lobes (3.6%) from dogs receiving silver-coated endotracheal tubes (p<0.001). Similarly, the second observer (MEO) scored 17 of 33 lung lobes (51.5%) and none of 28 lung lobes (0.0%) from the same groups of animals, respectively, as having large numbers of interstitial neutrophils (p<0.001). The K statistic for agreement between these two observers was 0.3642 (p=0.005) for scoring neutrophil infiltration in the alveolar walls and capillaries.

Correlation of Microbiological and Histologic Findings: A statistically significant correlation was found between the concentration of aerobic bacteria in the lung tissue specimens and the observed histology scores (Spearman rank correlation coefficient, 0.430; p<0.001, see FIG. 3). Similarly, a statistically significant correlation was found between the concentration of *P. aeruginosa* in the lung tissue specimens and the observed histology scores (Spearman rank correlation coefficient, 0.356; p=0.005).

Example 17

Rabbit Study

A study was conducted in rabbits to assess whether silver-coated endotracheal tubes reduce the colonization and migration of a bacteria challenge as compared to non-coated tubes. Observations were also made regarding the biocompatibility of the silver-coated device.

12 adult female New Zealand White rabbits were anesthetized and intubated with 3 mm inner diameter (ID) endotracheal tubes. Six rabbits received endotracheal tubes (referred to throughout this application as ETTs or ET tubes) coated with a polymer coating in which the polymer was 50% PVC and 50% polyurethane. The coating contained 5% colloidal silver chloride by weight. (The tubes were coated using procedures essentially identical to those of EXAMPLE 25). Six additional rabbits served as a control group and received ETTs that were identical to these tubes except that they were not coated. The tube's exterior within the oral cavity of the rabbits was inoculated at 0 and 6 hours with a respiratory *P. aeruginosa* isolate (PAO1, 1 ml each time, $9 \times 10^9$ CFU/ml in a saline solution). Subjects were positions to prevent the inocula from draining down the tube. The animals were maintained under anesthesia for 16 hours without incident and sacrificed. The endotracheal tube and adjacent trachea distal to the larynx were aseptically removed by dissection. Samples of the proximal (ventilator end), middle, and distal (patient end) portions from both the endotracheal tubes and tracheal tissue and were taken for quantitative microbiology (total aerobic bacteria and *P. aeruginosa*).

The proximal 1 centimeter, middle 1 cm, and distal 1 cm of the trachea in contact with the endotracheal tube for each animal were removed and placed in 1 ml of phosphate buffered saline. These samples were sonicated for 5 minutes then diluted 10-fold in PBS. The solutions were plated on tryptic soy agar and *Pseudomonas* isolation agar.

The proximal 1 centimeter, middle 1 cm, and distal 1 cm of each endotracheal tube were removed and placed in 1 ml of phosphate buffered saline. The lumen of the tube was disinfected with a 70% alcohol soaked swab. These samples were sonicated for 5 minutes then 10-fold diluted in PBS. The solutions were plated on tryptic soy agar and *Pseudomonas* isolation agar.

A lung sample from each animal was collected in a pre-weighed vial containing 1 ml of phosphate buffered saline. The samples were sonicated for 5 minutes then 10-fold diluted in PBS. The solutions were plated on tryptic soy agar and *Pseudomonas* isolation agar.

Samples of trachea and endotracheal tube were also collected for visualization under a scanning electron microscope.

Bacterial burden was determined by manual plate count. Bacterial burden on the proximal, middle, and distal samples from the tubes and trachea were found to be not statistically different by the F test for analysis of variance. Accordingly, the proximal, medial, and distal samples were grouped for subsequent analysis. The histopathology of tracheal samples was also assessed.

For *P. aeruginosa*, 6/6 of the control tubes were colonized compared to 2/6 of the silver-coated tubes. As well, 6/6 of the control rabbits' tracheal tissues were colonized compared to 3/6 of the test rabbits. *P. aeruginosa* had migrated to the lung tissue of 4/6 control rabbits, but no (0/6) test rabbits showed *P. aeruginosa* in the lungs. Histopathology of the control rabbit tracheas consistently demonstrated large numbers of inflammatory cells (polymorphonuclear leukocytes or PMNs) and blunted cilia. For the test rabbits, only one rabbit was characterized by having large numbers of inflammatory cells (PMNs), two rabbits had PMNs with intact epithelium, and three rabbits were characterized as having normal tissue. Histopathology observations appear in Table 2. Bacteria counts appear in Tables 3 and 4.

TABLE 2

Histopathology of tracheal samples removed from rabbits

| Rabbit ID | Histopathology Description |
|---|---|
| 1 Uncoated | Large numbers of inflammatory cells (PMN's) within the lumen of the trachea. Inflammatory cells present between the ciliated columnar epithelial cells and in the submucosal space. Cilia are blunt and in some cases sparse. |
| 2 Uncoated | Inflammatory cells (PMN's) within the lumen of the trachea. Inflammatory cells present between the ciliated columnar epithelial cells and in the submucosal space. Cilia are blunt and in some cases sparse. |
| 3 Uncoated | Large numbers of inflammatory cells (PMN's) within the lumen of the trachea. Inflammatory cells present between the ciliated columnar epithelial cells and in the submucosal space. Some tracheal areas denuded of epithelial cells. Cilia are blunt and in some case sparse. |
| 4 Uncoated | Large numbers of inflammatory cells (PMN's) within the lumen of the trachea. Inflammatory cells present between the ciliated columnar epithelial cells and in the submucosal space. Many tracheal erosions are evident and there is extensive PMN infiltration at these sites. Cilia are blunt and in some cases sparse. |
| 5 Uncoated | Large numbers of inflammatory cells (PMN's) within the lumen of the trachea. Inflammatory cells present between the ciliated columnar epithelial cells and in the submucosal space. Many tracheal erosions are evident and there is extensive PMN infiltration at these sties. Cilia are blunt and in some cases sparse. |
| 6 Uncoated | Large numbers of inflammatory cells (PMN's) within the lumen of the trachea. Much of the epithelial lining is absent Inflammatory cells present in the submucosal space. Many tracheal erosions are evident and there is extensive PMN infiltration at these sites. Cilia are blunt and In some cases sparse |
| 7 Coated | Inflammatory cells (PMN's) within the lumen of the trachea. Epithelial lining is intact and there are no erosions. Occasional inflammatory cells present in the submucosal space. Cilia are blunt and in some case sparse. |
| 8 Coated | Inflammatory cells (PMN's) within the lumen of the trachea. Epithelial lining is intact and there are no erosions. Occasional inflammatory cells present in the submucosal space. Cilia are blunt and in some case sparse. |
| 9 Coated | The tissue appears normal. |
| 10 Coated | The tissue appears in general normal. Occasional Inflammatory cells (PMN's) within the lumen of the trachea. |
| 11 Coated | The tissue appears normal. |
| 12 Coated | Large numbers of inflammatory cells (PMN's) within the lumen of the trachea. Much of the epithelial lining is absent. Inflammatory cells present in the submucosal space. Many tracheal erosions are evident and there is extensive PMN infiltration at these sites. Cilia are blunt and in some cases sparse |

TABLE 3

Total bacterial Counts on Endotracheal Tube, Trachea and Lung
Total Bacterial Count (TSA)

| Rabbit | Endotracheal Tube (cfu/cm) | | | Trachea (cfu/cm) | | | Lung (cfu/g) |
|---|---|---|---|---|---|---|---|
| | Proximal | Mid | Distal | Proximal | Mid | Distal | |
| 1 (control) | 3.0e6 | 1.9e6 | 8.0e5 | 1.7e5 | 1.0e5 | 7.0e5 | 4.0e5 |
| 2 (control) | 1.8e4 | 1.9e4 | 3.4e5 | 3.5e4 | 2.1e4 | 1.4e4 | 5.8e5 |
| 3 (control) | 1.9e4 | 4.0e4 | 4.4e4 | 1.0e6 | 6.0e5 | 5.5e5 | 4.5e5 |
| 4 (control) | 2.4e5 | 2.9e5 | 1.2e6 | 4.4e5 | 7.3e4 | 6.0e4 | 1.0e5 |
| 5 (control) | 6.4e5 | 6.6e5 | 1.9e6 | 6.2e5 | 3.0e4 | 3.1e4 | 2.9e5 |
| 6 (control) | 4.0e4 | 2.5e6 | 2.5e5 | 1.5e5 | 2.4e4 | 1.4e5 | NG |
| 7 (test) | 1.4c3 | 2.0e4 | 1.9e3 | 6.0e2 | 7.9e3 | 2.4e2 | NG |
| 8 (test) | 1.3e2 | NG | NG | 1.9e3 | 2.2e3 | 1.4e2 | NG |
| 9 (test) | NG | NG | NG | NG | NG | NG | NG |
| 10 (test) | 8.0e3 | 7.5e4 | 2.2e4 | 1.7e5 | 1.0e5 | 3.0e5 | NG |
| 11 (test) | NG | NG | NG | NG | NG | NG | NG |
| 12 (test) | 5.0e2 | 7.5e2 | 3.5e3 | 2.0e3 | 1.1e5 | 9.0e5 | NG |

TABLE 4

*Pseudomonas* Counts on Endotracheal Tube, Trachea and Lung
*Pseudomonas* Count (PIA)

| Rabbit | Endotracheal Tube (cfu/cm) | | | Trachea (cfu/cm) | | | Lung (cfu/g) |
|---|---|---|---|---|---|---|---|
| | Proximal | Mid | Distal | Proximal | Mid | Distal | |
| 1 (control) | 1.0e5 | 7.0e5 | 6.6e5 | 4.0e4 | 5.0e4 | 1.1e4 | 2.0e3 |
| 2 (control) | 3.9e2 | 4.4e3 | 7.2e3 | 3.1e4 | 4.5e3 | 1.2e4 | NG |
| 3 (control) | 1.0e3 | 6.0e3 | 4.2e3 | 1.9e3 | 1.1e3 | 9.4e2 | 1.6e3 |
| 4 (control) | 1.0e3 | 2.4e3 | 5.5e4 | 4.0e4 | 3.3e4 | 6.7e3 | 5.6c3 |
| 5 (control) | 2.7e3 | 3.6e4 | 3.0e4 | 4.2e3 | 7.7e3 | 1.1e2 | 4.3e4 |
| 6 (control) | NG | 5.0e4 | 5.0e3 | 1.5e3 | 6.5e3 | 3.8e4 | NG |
| 7 (test) | 7.0e2 | 1.1e2 | 2.0e2 | 1.0e2 | 3.5e2 | 5.5e2 | NG |
| 8 (test) | NG | NG | NG | NG | NG | NG | NG |
| 9 (test) | NG | NG | NG | NG | NG | NG | NG |
| 10 (test) | 3.1e3 | 2.4e4 | 8.5e3 | 4.5e4 | 2.5e4 | 4.5e4 | NG |
| 11 (test) | NG | NG | NG | NG | NG | NG | NG |
| 12 (test) | NG | NG | NG | 2.5e2 | 2.0e2 | 1.0e2 | NG |

Numbers are presented in exponential notation. For example, "5.0e2" refers to $5 \times 10^2$.

Table 5 summarizes the quantitative microbiological findings for which $\log_{10}$ reductions of 2-4 were measured for the groups receiving the silver-coated ETTs.

TABLE 5

| | Aerobic Bacteria[a] | | | *Pseudomonas*[a] | | |
|---|---|---|---|---|---|---|
| | ETT | Trachea | Lung | ETT | Trachea | Lung |
| Non-coated | 5.42 ± 0.78 | 5.08 ± 0.61 | 4.58 ± 2.26 | 3.84 ± 1.33 | 3.83 ± 0.72 | 2.48 ± 1.99 |
| Silver-coated | 1.95 ± 1.90 | 2.66 ± 2.20 | 0.54 ± 1.32 | 1.05 ± 1.62 | 1.54 ± 1.77 | 0.00 ± 0.00 |
| p Values[b] | <0.0001 | 0.0010 | 0.0167 | <0.0001 | 0.0004 | 0.0208 |

[a]Mean ± SD for $\log_{10}$ CFU per cm tube or gram tissue.
[b]Mann-Whitney Rank Sum test.
Based on the histopathology of the two groups, the coating did not appear to adversely affect host tissue.

Example 18

In Vitro Microbial Adherence Studies

Microbial adherence assays were performed on coated tubes with different silver levels and adherence was compared to a non-coated PVC ET tube. The coating was a polymer composition of 50% PVC and 50% polyurethane with silver present as colloidal silver chloride (prepared from silver nitrate and sodium chloride). The first step in device colonization is adherence of organisms to the surface, and this step occurs in a relatively short time (minutes). The assay assesses microbial adherence relative to a non-coated control by exposing portions of the tubes to high concentrations of various organisms ($10^8$-$10^9$ CFU/ml) for 2 hours. An alternative procedure is used for *Candida* because their adherence occurs slowly and with few organisms. Coated samples of known size are prepared from coated endotracheal tubes and compared with uncoated controls.

Procedure for Organisms Other than *Candida*

Cultures were prepared for each organism as follows. 200 ml of sterile media was inoculated with bacteria from a starter culture. Bacteria were then grown in Trypticase Soy Broth at 37±1° C. on a rotary shaker (approximately 150 rpm) for 12-18 hours. Cells were harvested by centrifugation for approximately 10 minutes at 4000×g at approximately 25° C., then washed twice using approximately 30 ml of 0.9% saline and centrifugation as described above.

Cells were suspended in minimal broth and adjusted to an optical density at 600 nm corresponding to a cell density of approximately $2 \times 10^8$ cells/ml. This suspension was then incubated at 37±1° C. with rotary shaking (approximately 150 rpm) for 1 hour±10 minutes. L-[3, 4, 5$^{-3}$H]-leucine was then added at a volume of 0.05% of the volume of the cell suspension (e.g., 20 μl leucine would be added to 40 ml of cell suspension). Incubation was continued for an additional 20±5 minutes. Cells were harvested and washed twice using approximately 30 ml of 0.9% saline and centrifugation at 4000×g at approximately 25° C. The pellet was then suspended in 0.9% PBS to a final concentration of approximately $10^8$ cells/ml.

Samples (coated and uncoated) were incubated with rotary shaking (~150 rpm) for 2 hours in the radiolabeled cell suspension at 37±2° C. The volume of cell suspension completely covered the sample. At the end of incubation, samples were immersed five times (approximately 1 second each time) in each of three successive volumes (approximately 160 ml) of 0.9% saline. Excess saline was then shaken from each piece and samples were placed in separate 20 ml glass scintillation vials containing 10 ml Opti-Fluor7 scintillation cocktail (Packard Instrument Co.). DPM was measured in each vial using a liquid scintillation counter (LS-5801, Beckman Instruments).

The number of organisms, as colony-forming units (CFU), corresponding to the radioactivity (DPM) was determined by serially diluting and plating labeled organisms and determining the radioactivity of the sample in DPM. A calibration chart was first prepared by measuring the DPM of samples containing a known number of radiolabeled CFU. The calibration chart was then used to convert DPM measurements to CFU. Microbial adherence is reported below for all samples (other than *Candida* spp.) as CFU per surface area of the device sample (CFU/mm$^2$). Within each testing batch, the coated samples are compared to the non-coated samples, and a percent reduction in adherence is determined.

Procedure Used for *Candida* spp.

Cultures were prepared for *Candida* species as follows. 200 ml of sterile media was inoculated with cells from a starter culture. Cells were then grown in Sabouraud Dextrose Broth (SDB) at 25±1° C. in a rotary shaker (approximately 150 rpm) for 24 hours. Cells were harvested by centrifugation for approximately 10 minutes at 4000×g at approximately 25° C., then washed twice using approximately 30 ml of 0.9% saline and centrifugation as described above.

Test samples were prepared for each suspension by cutting pieces of the tube. Samples were incubated with rotary shaking (~150 rpm) for 18 hours in the cell suspension at 37±2° C. The volume of cell suspension was sufficient to completely cover the sample. At the end of incubation, samples were removed and immersed five times (approximately 1 second each time) in each of three successive volumes (approximately 160 ml) of 0.9% saline. Excess saline was shaken from each piece and the rinsed test samples were each transferred into corresponding vials of PBS containing L-[3, 4, 5-$^3$H]-leucine at a volume of 0.05% of the total media volume and incubated at 37±1° C. with rotary shaking (approximately 150 rpm) for 30±5 minutes.

At the end of incubation, each test piece was immersed five times (approximately 1 second each time) in each of three successive volumes (approximately 160 ml) of 0.9% Saline. Excess saline was shaken from each piece and each piece was placed in separate 20 ml glass scintillation vials containing 10 ml Opti-Fluor7 scintillation cocktail (Packard Instrument Co.). DPM was measured in each vial with a liquid scintillation counter, (LS-5801, Beckman Instruments). Data was corrected for background decay. For *Candida*, adherence values are in scintillation units of DPM, rather than CFU.

Microorganisms relevant to the study of respiratory infections were used in the assay. Clinical isolates from airway and sputum samples from hospital laboratories and American Type Culture Collection (ATCC) were used. Greater differences in adherence were seen in organisms that adhere in greater numbers. Table 6 below summarizes the results.

TABLE 6

Summary of In Vitro Microbial Adherence Studies

| Score | Comparison to Non-Coated ETT |
|---|---|
| 2 | Statistically less adherence on Silver-Coated ETT, >90% reduction |
| 1 | Statistically less adherence on Silver-Coated ETT, >range 30%-90% reduction |
| 0 | Statistically equivalent adherence |
| −1 | Statistically greater adherence to Silver-Coated ETTs |

| | | | Performance | | |
|---|---|---|---|---|---|
| Organism | ID# | Non-coated CFU/mm$^2$ | Silver[a] 5.5 μg/cm$^2$ | Silver[a] 13.0 μg/cm$^2$ | Silver[a] 20.4 μg/cm$^2$ |
| *Pseudomonas aeruginosa* | ATCC 27853 | 3.91 × 10$^5$ | 2 | 2 | 2 |
| *Pseudomonas aeruginosa* | NGH 52461-02 | 3.62 × 10$^5$ | 2 | 2 | 2 |
| *Pseudomonas aeruginosa* | ATCC 27318 | 2.36 × 10$^5$ | 2 | 2 | 2 |
| *Pseudomonas aeruginosa* | GSU-3 | 1.39 × 10$^5$ | 2 | 2 | 2 |
| *Pseudomonas aeruginosa* | ATCC 17831 | 1.38 × 10$^5$ | 2 | 2 | 2 |
| MRSA | U Cinn | 4.05 × 10$^4$ | 1 | 1 | 1 |
| *Enterobacter cloacae* | U Cinn | 1.93 × 10$^4$ | 1 | 1 | 1 |
| *Enterobacter aerogenes* | ATCC 13048 | 1.50 × 10$^4$ | 1 | 1 | 1 |
| *Staphylococcus aureus* | ATCC 700698 | 1.34 × 10$^4$ | 1 | 1 | 1 |
| *Klebsiella pneumoniae* | ATCC 8047 | 1.13 × 10$^4$ | 1 | 0 | 1 |
| *Enterobacter aerogenes* | U Cinn | 9.06 × 10$^3$ | 1 | 1 | 1 |
| *Acinetobacter baumannii* | U Cinn | 5.29 × 10$^3$ | 1 | 0 | 0 |
| *Klebsiella pneumoniae* | NGH 52461-03 | 3.18 × 10$^3$ | 1 | 0 | −1 |
| *Serratia marcescens* | ATCC 43422 | 2.84 × 10$^3$ | 1 | 0 | 0 |
| *Enterobacter cloacae* | NGH 52287 | 2.43 × 10$^3$ | 0 | −1 | −1 |
| *Acinetobacter* | ATCC 19001 | 2.05 × 10$^3$ | 1 | 1 | 1 |
| *Acinetobacter* | ATCC 27251 | 2.02 × 10$^3$ | 0 | 1 | 0 |
| *Enterobacter aerogenes* | NGH 52328 | 1.67 × 10$^3$ | 0 | 0 | 0 |
| *Candida albicans* | ATCC 11651 | N/A | 0 | 0 | 0 |
| *Candida albicans* | ATCC 32089 | N/A | 0 | 0 | 0 |
| *Candida glabrata* | ATCC 38326 | N/A | 0 | 0 | −1 |

Silver levels result from original dipping solutions containing 2.5, 5.0, and 7.5% silver, respectively.
NGH, GSU, and U. Cinn. refer to clinical isolates from, respectively: Newton General Hospital, Covington, Georgia; Georgia State University; and the University of Cincinnati.
"MRSA" refers to Methicillin-resistant *S. aureus*.

Example 19

Zone of Inhibition Testing

Zone of inhibition testing was performed to demonstrate the low migration of silver ions from a coating containing colloidal silver chloride. This is an important factor in considering whether silver from could move down into the lungs. Test samples of a PVC tube were coated with a polymer containing 50% polyurethane/50% PVC containing colloidal silver chloride in three concentrations: greater than 30 μg/cm$^2$); 13 μg/cm$^2$; and 5.5 μg/cm$^2$. Using sterile scissors and forceps, test samples were prepared from sections (¼" to ½" lengths) of each of the tubes. The tests were run in triplicate for each of the following organisms:

*Candida albicans*, ATCC 32089 and ATCC 11651.
*Enterobacter aerogenes*, NGH 52328
*Enterobacter cloacae*, NGH 52287
*Klebsiella pneumoniae*, ATCC 8047 and NGH 52461-03
*Pseudomonas aeruginosa*, ATCC 17831 and ATCC 27318
*Staphylococcus aureus* NGH 52461-01

Organisms were incubated onto sample plates using known methods. Samples were then placed onto plates, each of which had been cultured with one of the organisms. The plates were then incubated to allow growth of the organism.

After incubation each of the sample plates was examined for inhibition of growth of the test organism surrounding the test article. If inhibition of a test organism was noted, the distance from the edge of the sample to the closest visible colony was measured and the zone in millimeters (mm) was recorded. For each of the test organisms the enumeration plates (either the 1:100 dilution from the stock or the 1:1000 dilution from the stock) were recorded. The approximate starting count for each organism was recorded.

Results are as follows.

For samples with coating at greater than 30 μg/cm$^2$:
No zones of inhibition for any of the samples against the following:
*Enterobacter cloacae*-NGH 52287, *Enterobacter aerogenes*-NGH 5232, *Klebsiella pneumonia* (ATCC 8047 and NGH 52461-03).
Limited zones (for 1 of the 3 samples) were observed on *Staphylococcus aureus*-NGH 52461-01 (a 1 mm zone), *Pseudomonas aeruginosa*-ATCC 17831 (a 1 mm zone), and *Candida albicans*-ATCC 11651 (a 2 mm zone). Zones were observed on all three samples for *Candida albicans*-ATCC 32089 (2-3 mm zones) and *Pseudomonas aeruginosa*-ATCC 27318 (1 mm zones).

For samples with coating at 13 μg/cm$^2$:
No zones of inhibition for any of the samples against the following:
*Pseudomonas aeruginosa*-ATCC 17831, *Enterobacter cloacae*-NGH 52287, *Enterobacter aerogenes*-NGH 52328 and *Klebsiella pneumonia* (ATCC 8047 and NGH 52461-03).
Limited zones (for 1 of the 3 samples) were observed for *Staphylococcus aureus*-NGH 52461-01 (1 mm zone) and *Candida albicans*-ATCC 11651 (1 mm zone).
Zones were observed for 2 of the 3 samples for *Candida albicans*-ATCC 32089 (1 mm zones) and *Pseudomonas aeruginosa*-ATCC 27318 (1 mm zones).

For samples with coating at 5.5 μg/cm$^2$:
No zones of inhibition for all three samples against the following:
*Candida albicans*-ATCC 11651, *Candida albicans*-ATCC 32089, *Enterobacter cloacae*-NGH 52287, *Enterobacter aerogenes*-NGH 52328, *Klebsiella pneumoniae*-ATCC 8047, *Klebsiella pneumoniae*-NGH 52461-03, *Pseudomonas aeruginosa*-ATCC 17831 and *Staphylococcus aureus*-NGH 52461-01.
Zones of 1 mm were observed on all three samples of *Pseudomonas aeruginosa*-ATCC 27318.

Example 20

Elution Testing and Microbial Adherence Testing after Elution Testing

Elution profile testing was conducted on ETTs to simulate and evaluate the release of the silver when exposed to body fluids. The incubation solution was 0.90% saline solution. Cuffed tracheal tubes made of PVC and having a diameter of 7.5 mm were obtained. The tubes were coated with a polymer coat in which the polymer was 50% PVC and 50% polyurethane. The coating also contained 5% colloidal silver chloride prepared by combining silver nitrate and sodium chloride (using the procedures of Example 25). Sterile coated tubes were cut into 1.0 cm pieces starting about 1 cm from edge of where the cuff is adhered. The ET tube pieces were separated as they were cut for assay of total silver, bacterial adherence after elution, and assay for total silver after elution. All total silver analyses (also referred to as "silver assays" "total silver assays") in this Example and anywhere else in this application involved verified assay methods.

Samples of coated tubes for total silver assay after elution and bacterial adherence after elution were placed into pre-heated vials (3 pieces per vial) containing the incubation solution and incubated for 1 hour at 37° C. in an oven. Pieces were then removed from the vials, drained on the inner vial walls, placed in a second set of vials, each containing 30 ml incubation solution, and incubated for another hour at 37° C., for a cumulative incubation time of 2 hours. Pieces were then removed from the vials, drained on the inner vial walls, placed in a third set of labeled, pre-heated vials containing 30 ml of the incubation solution, and incubated for 2 more hours at 37° C., for a cumulative incubation time of 4 hours. Pieces were then removed, drained on the inner vial walls, placed in a fourth set of labeled, pre-heated vials containing 30 ml incubation solution and incubated for 4 more hours in an oven at 37° C., for a cumulative incubation time of 8 hours. Pieces were then removed from the fourth set of vials, drained on the inner vial walls, placed in a fifth set of labeled, pre-heated vials containing 30 ml incubation solution, and incubated for 16 more hours in an oven at 37° C., for a cumulative incubation time of 24 hours.

At the conclusion of 24 hours, three samples were removed and subjected to total silver analysis. At the same time, six samples were removed, dried, sterilized with ethylene oxide, and subjected to bacterial adherence testing using *Pseudomonas aeruginosa* pursuant to the procedures in Example 18 above. All other samples were removed from the vials, drained on the inner vial walls, placed in another set of vials, each containing 30 ml incubation solution, and incubated for another 48 hours (two days) at 37° C., changing incubation solution daily, for a cumulative incubation time of three days.

At the conclusion of three days, three samples were removed and subjected to total silver analysis. At the same time, six samples were removed, dried, sterilized with ethylene oxide, and subjected to bacterial adherence testing using *Pseudomonas aeruginosa* pursuant to the procedures in Example 18 above. All other samples were removed from the vials, drained on the inner vial walls, placed in another set of vials, each containing 30 ml incubation solution, and incubated for another 96 hours (four days) at 37° C., changing incubation solution daily, for a cumulative incubation time of seven days.

At the conclusion of seven days, three samples were removed and subjected to total silver analysis. At the same time, six samples were removed, dried, sterilized with ethylene oxide and subjected to bacterial adherence testing using *Pseudomonas aeruginosa* pursuant to the procedures in Example 18 above. All other samples were removed from the vials, drained on the inner vial walls, placed in another set of vials, each containing 30 ml incubation solution, and incubated for another 168 hours (7 days) at 37° C., changing incubation solution daily, for a cumulative incubation time of 14 days.

At the conclusion of 14 days, three samples were removed and subjected to total silver analysis. At the same time, six samples were removed, dried, sterilized with ethylene oxide, and subjected to bacterial adherence testing using *Pseudomonas aeruginosa* pursuant to the procedures in Example 18 above. All other samples were removed from the vials, drained on the inner vial walls, placed in another set of vials, each containing 30 ml incubation solution, and incubated for another 168 hours (7 days) at 37° C., changing incubation solution daily, for a cumulative incubation time of 21 days.

At the conclusion of 21 days, three samples were removed and subjected to total silver analysis. At the same time, the six remaining samples were removed, dried, sterilized with ethylene oxide, and subjected to bacterial adherence testing using *Pseudomonas aeruginosa* pursuant to the procedures in Example 18 above.

Samples that were not eluted were also assayed using total silver analysis. These non-eluted samples provided the initial (pre-elution) silver concentration values for each tube.

Total Silver Analysis results were used to calculate silver loss for each tube at each interval. The percent loss of silver was calculated by dividing the concentration of silver remaining on the soaked pieces by the initial silver concentration and multiplying the result by 100. Results are presented in Table 7.

TABLE 7

% Silver Loss and Supporting Data

| Time | Conc.(ug/cm$^2$) | After Soak.(ug/cm$^2$) | % Loss |
|---|---|---|---|
| 24 hours | 12.61 | 7.79 | 38.23 |
| 3 days | 13.42 | 5.33 | 60.31 |
| 7 days | 14.21 | 2.19 | 84.57 |
| 14 days | 14.47 | 3.71 | 74.40 |
| 21 days | 13.28 | 2.63 | 80.20 |

The saline elution model indicates that after 14 days approximately 25% of the silver remains.

Figure 5:
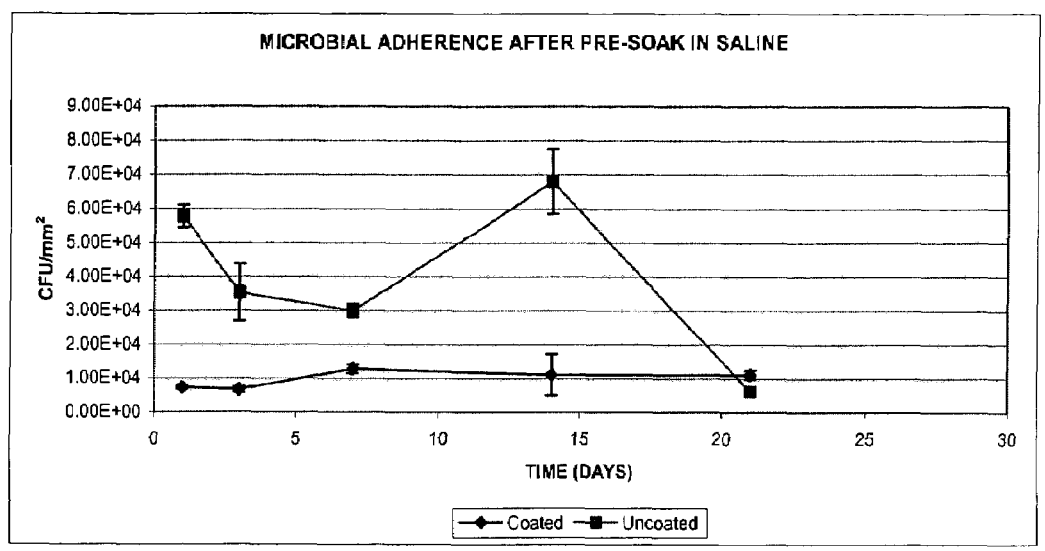
FIG. 5 depicts plots of microbial adherence values of endotracheal tubes coated with a coating of the present invention and uncoated endotracheal tubes. The raw data upon which the plots are based appear in Example 20 herein.

Uncoated tubes were then prepared for comparison of microbial adherence by subjecting them to the same elution procedures as for the test samples Results of the bacterial adherence testing after saline elution of the samples for 1, 3, 7, 14, and 21 days are shown in Table 8 and appear in the graph set forth in FIG. 5.

TABLE 8

| | Mean CFU/mm$^2$ | | Standard deviation | |
|---|---|---|---|---|
| Day | Uncoated | Coated | Uncoated | Coated |
| 1 | 5.78E+04 | 7.27E+03 | 3.29E+03 | 5.57E+02 |
| 3 | 3.53E+04 | 6.66E+03 | 8.41E+03 | 9.33E+02 |
| 7 | 3.00E+04 | 1.28E+04 | 2.07E+03 | 1.26E+03 |
| 14 | 6.80E+04 | 1.12E+04 | 9.48E+03 | 6.09E+03 |
| 21 | 6.26E+03 | 1.12E+04 | 1.02E+03 | 1.32E+03 |

All saline-eluted coated samples were found to have better microbial adherence performance, i.e., reduced microbial adherence in terms of CFU/mm$^2$, as compared to uncoated controls for up to 14 days of elution.

Example 21

Coefficient of Friction Testing

Sixty (60) coated and sixty uncoated samples of each type and diameter tube were used in this testing and testing was conducted in pairs, resulting in 30 data points per tube size. Substrate tubes were PVC. For coated tubes, the coating was a polymer solutions in which the polymers were 50% PVC and 50% polyurethane. The coating also contained silver in a concentration of 5%, present as colloidal silver chloride. Coefficient of friction (COF) was determined by measuring the force needed to draw an object resting on a pair of tubes along a portion of the length of those two tubes. In each test, a pair of identical samples previously hydrated in water at 37° C. for 1 hour, 1 day, 7 days, 14 days or 21 days, was placed in a trough of 37° C. water. A stainless steel sled weighing 390 grams and having a flat bottom surface and horizontal dimensions of 2.5 inches by 2.5 inches was wrapped with a cellulose membrane (dialysis tubing, Spectrapor #1, Spectrum Medical Industries, Inc.). The sled was then pulled mechanically in a longitudinal direction along the surfaces of the pairs of samples for a distance of approximately 5 inches at a constant rate of 6 inches/minute. The force required to pull the sled at this rate was recorded continuously and averaged over the test period the sled was pulled. Force measurements used a Chatillon Model DGGHS force gauge. Pull force data points were measured in grams and divided by the weight of the sled to generate a unitless coefficient of friction number. The COF numbers are averaged to give an average COF value for the thirty data points. Results for the uncoated (U/C) and coated (C) tubes are present in Table 9.

TABLE 9

COEFFICIENT OF FRICTION DATA

| Type | 1 hr. | 1 day | 7 days | 14 days | 21 days |
|---|---|---|---|---|---|
| | | 6.0 mm inner diameter tubes | | | |
| U/C | 0.277 ± 0.125 | 0.292 ± 0.034 | 0.414 ± 0.079 | 0.430 ± 0.074 | 0.297 ± 0.047 |
| C | 0.360 ± 0.031 | 0.347 ± 0.035 | 0.298 ± 0.032 | 0.292 ± 0.030 | 0.246 ± 0.025 |
| | | 7.5 mm inner diameter tubes | | | |
| U/C | 0.342 ± 0.060 | 0.350 ± 0.065 | 0.347 ± 0.054 | 0.315 ± 0.066 | 0.328 ± 0.057 |
| C | 0.337 ± 0.042 | 0.336 ± 0.034 | 0.262 ± 0.033 | 0.226 ± 0.037 | 0.231 ± 0.035 |

TABLE 9-continued

COEFFICIENT OF FRICTION DATA

| Type | 1 hr. | 1 day | 7 days | 14 days | 21 days |
|---|---|---|---|---|---|
| | | 10.0 mm inner diameter tubes | | | |
| U/C | 0.332 ± 0.076 | 0.318 ± 0.059 | 0.317 ± 0.059 | 0.272 ± 0.069 | 0.299 ± 0.063 |
| C | 0.373 ± 0.037 | 0.269 ± 0.031 | 0.200 ± 0.023 | 0.161 ± 0.030 | 0.138 ± 0.039 |

Example 22

Samples containing different concentrations of silver salts in the coatings were prepared to evaluate the effect of different concentrations of silver salts in the coating used on endotracheal (ET) tubes. PVC endotracheal tubes were coated with a polymer coating in which 50% of the polymer was PVC and 50% was polyurethane. The coatings were prepared with colloidal silver chloride by adding silver nitrate and sodium chloride. Coatings were prepared containing 1%, 2.5%, 5%, 10%, and 15% silver by dry coating weight. Uncoated samples and samples with coatings containing each of these silver concentrations were tested for coefficient of friction (COF) using the procedures of Example 21, above; zone of inhibition, using the procedures of Example 19, above; and microbial adherence using the procedures of Example 18, above. Total Silver Analysis was also performed using validated methods.

COF Results

Testing was performed on endotracheal tubes from each dosage concentration after a 1 hr, 1 day, 7 day, 14 day, and 21 day soak in heated water. Results are presented in Table 10.

TABLE 10

Coefficient of Friction for Different Concentrations After Soaking for Different Periods of Time

| CONC | 1 hr. | 1 day | 7 days | 14 days | 21 days |
|---|---|---|---|---|---|
| 1% | 0.140 ± 0.020 | 0.133 ± 0.023 | 0.095 ± 0.004 | 0.104 ± 0.008 | 0.101 ± 0.012 |
| 2.5% | 0.215 ± 0.023 | 0.229 ± 0.022 | 0.152 ± 0.031 | 0.105 ± 0.016 | 0.107 ± 0.012 |
| 5% | 0.357 ± 0.051 | 0.368 ± 0.036 | 0.254 ± 0.026 | 0.172 ± 0.050 | 0.116 ± 0.023 |
| 10% | 0.373 ± 0.030 | 0.354 ± 0.019 | 0.230 ± 0.025 | 0.230 ± 0.020 | 0.229 ± 0.034 |
| 15% | 0.371 ± 0.026 | 0.380 ± 0.025 | 0.276 ± 0.017 | 0.309 ± 0.048 | 0.224 ± 0.016 |

Zone of Inhibition Results:
  The 1% concentration produced no zone of inhibitions against the following: *Pseudomonas aeruginosa, Staphylococcus aureus,* and *Candida albicans.*
  The 2.5% concentration produced no zone of inhibitions against the following: *Pseudomonas aeruginosa, Staphylococcus aureus,* and *Candida tropicalis.*
  The 5% concentration produced no zone of inhibitions against the following: *Pseudomonas aeruginosa,* and *Staphylococcus aureus. Candida tropicalis* produced a zone on one of three samples but was measured to be less than 1 mm.
  The 10% concentration produced no zone of inhibitions against the following: *Pseudomonas aeruginosa, Staphylococcus aureus,* and *Candida albicans.*
  The 15% concentration produced no zone of inhibitions against the following: *Pseudomonas aeruginosa,* and *Staphylococcus aureus. Candida tropicalis* produced a zone on two of three samples.

Bacterial Adherence Results:

Results in DPM and (except *Candida*) in CFU/mm$^2$ are presented in Table 11 through 15. All controls (referred to as "CONT" in the tables below) were uncoated silicone. Coated tubes are provided as "ET TUBE."

TABLE 11

Bacterial Adherence Data
*Staphylococcus aureus* ATCC 700698

| CFU/mm$^2$ | CONT | ET TUBE | 1.0% S | 2.5% S |
|---|---|---|---|---|
| 1 | 2.65E+04 | 4.27E+04 | 1.24E+04 | 1.27E+04 |
| 2 | 3.43E+04 | 3.84E+04 | 1.33E+04 | 1.14E+04 |
| 3 | 2.97E+04 | 3.87E+04 | 1.11E+04 | 1.28E+04 |
| 4 | 3.42E+04 | 3.72E+04 | 1.42E+04 | 1.16E+04 |
| 5 | 3.10E+04 | 4.36E+04 | 1.21E+04 | ?? |
| AVG | 3.11E+04 | 4.01E+04 | 1.26E+04 | 1.22E+04 |
| s.d. | 3.28E+03 | 2.83E+03 | 1.20E+03 | 7.22E+02 |

TABLE 12

Bacterial Adherence Data
*Pseudomonas aeruginosa* ATCC 17831

| CFU/mm$^2$ | CONT | ET TUBE | 1.0% S | 2.5% S |
|---|---|---|---|---|
| 1 | 3.55E+04 | 5.79E+04 | 1.00E+04 | 9.09E+03 |
| 2 | 4.42E+04 | 6.27E+04 | 9.14E+03 | 8.85E+03 |
| 3 | 3.93E+04 | 7.16E+04 | 9.59E+03 | 9.05E+03 |
| 4 | 4.03E+04 | 8.52E+04 | 8.62E+03 | 1.21E+04 |
| 5 | 3.93E+04 | 7.87E+04 | 9.30E+03 | 7.67E+03 |
| AVERAGE | 3.97E+04 | 7.12E+04 | 9.33E+03 | 9.35E+03 |
| s.d. | 3.11E+03 | 1.12E+04 | 5.15E+02 | 1.65E+03 |

TABLE 13

Adherence Data
C. albicans ATCC 11651

|  | CONT | ET TUBE | 2.5% S | 5% S | 10% S | 15% S |
|---|---|---|---|---|---|---|
| DPM | | | | | | |
| #1 | 184381 | 640012 | 26935 | 36675 | 26708 | 24970 |
| #2 | 116794 | 512099 | 35359 | 24761 | 26694 | 16840 |
| #3 | 174946 | 273695 | 28715 | 11643 | 26084 | 21918 |
| #4 | 200527 | 618035 | 22848 | 23747 | 26018 | 22977 |
| #5 | 107633 | 273231 | 28576 | 23195 | 16054 | 22027 |
| Background | 55 | 46 | 55 | 51 | 54 | 53 |
| Surface Area (mm$^2$) | 428 | 560 | 560 | 560 | 560 | 560 |
| DPM/mm$^2$ | | | | | | |
| #1 | 430.668 | 1142.796 | 48 | 65.4 | 47.596 | 44.495 |
| #2 | 272.755 | 914.380 | 63.043 | 44.125 | 47.571 | 29.977 |
| #3 | 408.624 | 488.659 | 51.179 | 20.7 | 46.482 | 39.045 |
| #4 | 468.393 | 1103.552 | 40.702 | 42.314 | 46.364 | 40.936 |
| #5 | 251.350 | 487.830 | 50.930 | 41.329 | 28.571 | 39.239 |
| Average | 366.358 | 827.444 | 50.771 | 42.774 | 43.317 | 38.738 |
| s.d. | 97.879 | 321.463 | 8.060 | 15.838 | 8.264 | 5.36 |

TABLE 14

Bacterial Adherence Data
Staphylococcus aureus ATCC 700698

| CFU/mm2 | CONT | ET TUBE | 2.5% S | 5% S | 10% S | 15% S |
|---|---|---|---|---|---|---|
| 1 | 1.05E+04 | 2.64E+04 | 9.13E+03 | 1.17E+04 | 1.21E+04 | 1.57E+04 |
| 2 | 2.35E+04 | 2.65E+04 | 9.81E+03 | 1.15E+04 | 1.11E+04 | 1.24E+04 |
| 3 | 1.42E+04 | 2.52E+04 | 1.02E+04 | 1.31E+04 | 1.60E+04 | 1.32E+04 |
| 4 | 1.38E+04 | 2.76E+04 | 9.86E+03 | 1.12E+04 | 1.64E+04 | 1.47E_04 |
| 5 | 1.71E+04 | 2.27E+04 | 1.21E+04 | 1.27E+04 | 1.28E+04 | 1.26E+04 |
| AVG | 1.58E+04 | 2.57E+04 | 1.02E+04 | 1.20E+04 | 1.37E+04 | 1.37E+04 |
| s.d. | 4.92E+03 | 1.86E+03 | 1.14E+03 | 8.21E+02 | 2.36E+03 | 1.44E+03 |

TABLE 15

Bacterial Adherence Data
Pseudomonas aeruginosa ATCC 17831

| CFU/mm$^2$ | CONT | ET TUBE | 2.5% S | 5% S | 10% S | 15% S |
|---|---|---|---|---|---|---|
| 1 | 4.62E+04 | 1.04E+05 | 8.96E+03 | 8.89E+03 | 9.01E+03 | 5.57E+03 |
| 2 | 5.86E+04 | 1.09E+05 | 8.30E+03 | 8.47E+03 | 1.17E+04 | 8.19E+03 |
| 3 | 4.69E+04 | 1.12E+05 | 1.15E+04 | 8.38E+03 | 9.27E+03 | 7.90E+03 |
| 4 | 4.45E+04 | 1.18E+05 | 8.01E+03 | 8.10E+03 | 9.06E+03 | 6.55E+03 |
| 5 | 4.68E+04 | 1.07E+05 | 9.39E+03 | 1.12E+04 | 8.15E+03 | 1.59E+04 |
| AVG | 4.86E+04 | 1.10E+05 | 9.23E+03 | 9.01E+03 | 9.44E+03 | 8.81E+03 |
| s.d. | 5.67E+03 | 5.09E+03 | 1.38E+03 | 1.27E+03 | 1.33E+03 | 4.07E+03 |

Summary:
All concentrations tested were found to have reduced bacterial adherence against *Pseudomonas aeruginosa* when compared to a PVC control tube.
All concentrations tested were found to have reduced bacterial adherence against *Staphylococcus aureus* when compared to a PVC control tube.
All concentrations tested were found to have reduced bacterial adherence against *Candida albicans* when compared to a PVC control tube.

Total Silver Analysis results. The results (from on five samples for each concentration) are presented in Table 16.

TABLE 16

| % Silver | Silver measured in µg/cm$^2$ | Average µg/cm$^2$ (n = 5) |
|---|---|---|
| 1% | 2.01, 1.95, 2.00, 1.80, 2.18 | 1.99 |
| 2.5% | 5.37, 5.61, 5.42, 5.69, 5.92 | 5.60 |
| 5% | 12.81, 13.10, 11.85, 12.81, 12.87 | 12.69 |
| 10% | 29.95, 27.89, 28.13, 29.41, 28.74 | 28.82 |
| 15% | 44.80, 44.45, 49.89, 42.75, 48.08 | 46.00 |

Example 23

Exposure to Drugs and Chemicals

Testing was conducted to evaluate the interaction of the silver/hydrogel coating with various chemicals to which the device could be expected to come into contact during normal use.

Interaction with Nebulized Atropine Sulfate, Albuterol Sulfate, and Acetylcysteine Separate ET tubes were exposed to one of the following drugs: Atropine Sulfate, (NDC 10019-250-20), Albuterol Sulfate, USP, 0.083%, NDC 59930-1500-6, and Acetylcysteine, USP, NDC 0074-3308-03. These are drugs commonly used for respiratory therapy. In each case, the drugs were nebulized into a chamber containing a cuffed endotracheal tube coated using the procedures of EXAMPLE 25, below. The nebulizer system comprised a compressor, reservoir hose, 5-ml-medicine cup, and a T connector. The T connector was joined to a 2-liter jar modified to receive the T connector through the jar sidewall. The jar lid was modified to have a small port acting as a pressure relief valve. One end of the reservoir hose was connected to the hose port of a nebulizer. The coated tube was then placed into the 2-liter container, or chamber, and the lid was secured. The T connector was inserted into the 2-liter chamber, port located on the sidewall. 3 ml of the drug was placed into the 5-ml.-medicine cup. The loose end of the reservoir hose was placed in the underside of the 5-ml.-medicine cup. The nebulizer was then turned on, and run until all the drug had been nebulized. The nebulizer was then turned off, and the samples were allowed to remain in the chamber for 30 minutes after the nebulizer had been switched off. The test product was removed and rinsed using deionized (DI) water by dipping sample in clean DI water twice for a total of 10 seconds.

Coefficient of friction (COF) testing was performed on endotracheal tubes from each drug exposure using the procedures set forth in Example 21 above. COF results were collected after a 1 hr, 1 day, 7 day, 14 day, and 21 day soak in 37° C. water. Results are presented in Table 17.

TABLE 17

| Drug | 1 hr. | 1 day | 7 days | 14 days | 21 days |
|---|---|---|---|---|---|
| Acet. | 0.301 ± 0.037 | 0.154 ± 0.026 | 0.097 ± 0.002 | 0.090 ± 0.017 | 0.087 ± 0.017 |
| A.S. | 0.329 ± 0.024 | 0.192 ± 0.011 | 0.084 ± 0.009 | 0.079 ± 0.017 | 0.107 ± 0.030 |
| Albut | 0.275 ± 0.027 | 0.228 ± 0.021 | 0.076 ± 0.003 | 0.086 ± 0.016 | 0.108 ± 0.011 |

Acet. = Acetylcysteine
A.S. = Atropine sulfate
Albut. = Albuterol sulfate

The total silver was determined using verified techniques. Results are presented in Table 18.

TABLE 18

| | Total Silver Analysis |
|---|---|
| Drug | Silver Concentration ($\mu g/cm^2$) n = 3 |
| Acet. | 12.92 ± 0.69 |
| A.S. | 15.01 ± 3.85 |
| Albut. | 13.75 ± 0.67 |

Acet. = Acetylcysteine
A.S. = Atropine sulfate
Albut. = Albuterol sulfate

Exposure to Lidocaine Jelly, Lidocaine HCl, and Lubricating Jelly

Separate ET tubes were exposed to Lidocaine Jelly, Lidocaine HCl, and Lubricating Jelly. A container was filled with enough lidocaine jelly (2% lidocaine hydrochloride in a solution of water, hydroxypropylmethylcellulose, and preservatives or equivalent topical lidocaine containing formulation) such that when 3 ET tubes were immersed the jelly will cover the ET tubes 1 inch past the coating transition line. ET tubes were then immersed in the container filled with lidocaine jelly for approximately 30 minutes. The product was removed after soaking and excess lubricant was allowed to drain off surface of catheter. The product was rinsed using deionized (DI) water by immersing sample in clean DI water bath for 5 minutes and then in another fresh DI water bath for 1 minute. The same procedures were repeated using lidocaine HCl (2%) in water and K-Y® lubricating jelly.

Samples were visually inspected, tested for coefficient of friction using the procedures in Example 21 above, and subjected to total silver analysis using verified methods to determine whether exposure to these substances adversely affected these characteristics. No coating delamination, discoloration, or other affects were observed. Coefficient of friction testing was performed on endotracheal tubes from each drug exposure. COF results were collected after a 1 hr, 1 day, 7 day, 14 day, and 21 day soak in heated water. Results are presented in Table 19 below.

TABLE 19

| Drug | 1 hr. | 1 day | 7 days | 14 days | 21 days |
| --- | --- | --- | --- | --- | --- |
| Lube | 0.217 ± 0.021 | 0.164 ± 0.023 | 0.143 ± 0.022 | 0.086 ± 0.005 | 0.072 ± 0.004 |
| Lid. HCL | 0.327 ± 0.013 | 0.223 ± 0.021 | 0.092 ± 0.013 | 0.079 ± 0.004 | 0.084 ± 0.012 |
| Lid. Jelly | 0.370 ± 0.021 | 0.228 ± 0.032 | 0.097 ± 0.012 | 0.088 ± 0.008 | 0.107 ± 0.030 |

Lube = Lubricating jelly
Lid HCL. = Lidocaine HCl in water
Lid Jelly = Lidocaine Jelly Total silver analysis results are presented in Table 20 below.

TABLE 20

| Drug | Silver Concentration ($\mu g/cm^2$) n = 3 |
| --- | --- |
| Lube | 13.53 ± 3.24 |
| Lid. HCL | 14.37 ± 1.98 |
| Lid. Jelly | 14.62 ± 0.42 |

Lube = Lubricating jelly
Lid HCL. = Lidocaine HCl in water
Lid Jelly = Lidocaine Jelly
The ETT coating is not compromised when exposed to lubricating jelly.

Example 24

Magnetic Resonance Imaging Interaction Testing

Tests were conducted with coated endotracheal tubes to determine whether magnetic resonance (MR) such as that used in magnetic resonance imaging (MRI) would produce any effects that would be adverse to a patient in which such a tube was used. The samples included an endotracheal tube made from PVC coated with a polymer composition in which 50% of the polymer was PVC and 50% of the polymer was polyurethane. The coating contained silver chloride in amounts greater than 30 $\mu g/cm^2$. MR source was a 1.5 Tesla 64 MHz MR system (Sigma MR System, General Electric Medical Systems, Milwaukee, Wis.).

Magnetic Field Interaction.

Translational attraction testing was conducted using a "deflection angle test," which is described, for example, in American Society for Testing and Materials Method No. F 2052. Each individual ET tube was suspended by a 20-cm length of thin thread (weighing less than 5% the weight of the ET tube) and attached to a plastic protractor so that the angle of deflection from the vertical could be measured. The test was conducted at the position in the 1.5-Tesla MR system where the spatial gradient had been determined to be at a maximum in order to determine the translational attraction with regard to an extreme magnetic field exposure condition. It was found that the highest spatial gradient for the system used for testing occurs at an off-axis position that is 35-cm inside the opening of the bore of the system. The magnetic spatial gradient at this position was found to be 450 gauss per centimeter.

Evaluation was also performed to determine qualitatively the presence of magnetic field-induced torque for the ET tube. A flat plastic material with a millimeter grid on the bottom was used (coefficient of friction was 0.07). Each tube was placed on the test apparatus in an orientation that was 45 degrees relative to the static magnetic field of the MR system. The test apparatus with ET tube was then positioned in the center of the MR system, where the effect of torque from the static magnetic field was determined to be the greatest based on a previous magnetic field survey for the MR system. Each ET tube was directly observed for any possible movement with respect to alignment or rotation relative to the static magnetic field of the MR system. The observation process was facilitated by having the investigator inside of the bore of the MR system during the test procedure. The ET tube was then moved 45 degrees relative to its previous position and again observed for alignment or rotation. This process was repeated to encompass a full 360 degrees rotation of positions for ET tube in the MR system. The following qualitative scale of torque was applied to the results: 0, no torque; +1, mild or low torque, the implant slightly changed orientation but did not align to the magnetic field; +2, moderate torque, the implant aligned gradually to the magnetic field; +3, strong torque, the implant showed rapid and forceful alignment to the magnetic field; +4, very strong torque, the implant showed very rapid and very forceful alignment to the magnetic field.

Two tested samples were found to have a deflection angle of 4 degrees and a qualitative torque of zero. It was thus concluded that the tubes would have relatively minor MR field interactions and that use of the coated tubes would create no additional risk to a patient with respect to movement or dislodgment for the tested tube.

Heating Due to MRI

Heating due to MRI was then determined. An extreme radiofrequency (RF) power exposure experiment was performed with each ET tube placed inside of a specially-constructed, gel-filled phantom. A plastic phantom was prepared and filled with a semi-solid gel to simulate human tissue. The gelling agent was hydroxyethyl-cellulose (HEC) in an aqueous solution (91.48% water) along with 0.12% NaCl to create a dielectric constant of approximately 80 and a conductivity of 0.8 S/m at 64 MHz. The phantom had dimensions and configuration to approximate the size of the human torso. The phantom was constructed as a torso that is a 24" high by 17" wide rectangle with a protrusion centered in the top of the torso to simulate a head. The protrusion was 11.5 inches high and 6.5 inches wide. The torso lacked a flow to simulate blood flow and thus would be expected to experience a more localized heating effect than in the human body. The ET tube was fixed to a plastic frame to facilitate positioning in the phantom and MR system during the heating experiment. The Sigma system described above was used, and the body coil served to send and to receive RF energy.

A T1-weighted spin echo pulse sequence was used for imaging, as follows: total imaging time, 20 minutes; axial plane; 135 msec; echo time, 20 msec; field of view, 48 cm; imaging matrix, 256×128; section thickness, 20.0 mm; number of section locations, 4; number of excitations, 27; number of echoes, 4; phasing direction, anterior to posterior;

transmitter gain, 200. The pulse sequence produced a whole body average specific absorption rate (SAR) of 1.2 W/kg and a spatial peak SAR of 2.5 W/kg. This level of exposure exceeds that typically used for clinical MRI procedures.

Temperature recordings were obtained in this experiment using a Luxtron Model 3100 Fluoroptic Thermometry system previously demonstrated to be MRI-compatible and unperturbed at static magnetic field strengths up to 9.0-Tesla (i.e. an MR spectrometer). This thermometry system has small fiber-optic probes (0.5 mm diameter) that respond rapidly (response time, 0.25 seconds), with an accuracy and resolution of ±0.1° C. The ET tube that underwent assessment for MRI-related heating had two thermometry probes attached to record representative temperature during the experiment. The probes were placed: at 0.5 mm from the end of the ET tube (Probe #1); at 0.5 mm from the center of the ET tube (Probe #2); and in the gel-phantom at a position removed (approximately 40 cm away) from the ET tube to record a reference temperature during the heating experiment (Probe #3). The gel phantom with the ET tube and thermometry probes was placed inside of the MR system. The gel-filled phantom was allowed to equilibrate to the temperature of the environmental temperature for a period of one hour. The room temperature and temperature of the bore of the MR system were 20.6° C., with a relative humidity of 45%. The MR system fan was not on during the experiment. Baseline temperatures were recorded at 20-sec. Intervals for 5 minutes. MRI was then performed for 20 minutes with temperatures recorded at 20-sec. Intervals. The highest temperature changes were +0.5° C. for Probe #1, +0.5° C. for Probe #2, and +0.4° C. for Probe #3.

Induced Electrical Currents

A comprehensive analysis of the interaction of the ET tube with MRI time-varying fields was performed. Measurements were made with an HP digital multimeter using a pair of needle probes. The probes were pressed into the tubing to make good electrical contact. The following sections of the ET tube were checked: main tube, end connector, flue rod, and inflation cuff. All sections exhibited an impedance in excess of 1 MΩ when the voltmeter probes were 1 cm apart. Thus, the ET tube is essentially an insulator when compared to conductivity of tissue. The only conducting section of the tube is the spring at the end of the air tube. The spring has a length of about 7 mm, a diameter of about 3 mm and has about 7 turns. The wire has a radius of about 0.1 mm. The spring is covered by plastic insulating material of about 3 mm thickness. The resistance of the spring is calculated a approximately 0.21Ω. It was determined by calculation that RF-induced temperature rise may occur near the flanks and end of the tube that is approximately twice the background rise, but that this would be expected to be no more than will already occur due to the electrical heterogeneities in the body. RF-induced heating should be otherwise imperceptible. Heating by pulse gradient current would expect to result in a temperature rise less than 0.008° C.

Artifact Test

MRI artifacts were assessed for one sample of the ET tube. This test was accomplished by performing MR imaging with the ET tube placed inside of a gel-filled phantom. The phantom had a rectangular shape with the following dimensions: 30-cm width, 55-cm height, 75-cm length. The ET tube was attached to a plastic frame to facilitate positioning and MR imaging within this phantom. MR imaging was conducted using the Sigma system described above, with a send-receive body coil.

A T1-weighted spin echo pulse sequence was used for imaging, as follows: repetition time, 500 msec; echo time, 20 msec; field of view, 30 cm; matrix size, 256×256; section thickness, 5 mm; number of excitations, 2; bandwidth, 16 kHz. A gradient echo (GRE) pulse sequence was also used, repetition time, 100 msec; echo time, 15 msec; flip angle, 30 degrees; field of view, 30 cm; matrix size, 256×256; section thickness, 5 mm; number of excitations, 2; bandwidth, 16 kHz. The imaging planes were oriented to encompass the long axis and short axis of the ET tube. The frequency encoding direction was parallel to the plane of imagine. The planimetry software provided with the MR system was used to measure the cross-sectional areas for the artifacts associated with the ET tube. The accuracy of this planimetry method is ±10.

The artifacts that appeared on the MR images were shown as localized signal voids (i.e. signal loss) easily recognized on images. In general, the GRE pulse sequence produced larger artifacts that the T1-weighted, spin echo pulse sequence for the ET tube. It was concluded that the artifacts should not affect the function of MR systems unless the imaging area of interest is in the exact same position or close to the device. Results appear below in Table 21.

TABLE 21

Summary of MRI Artifact Information for ET Tube

| | | | | |
|---|---|---|---|---|
| Signal Void Size | 2,406 mm$^2$ | 161 mm$^2$ | 2,598 mm$^2$ | 184 mm$^2$ |
| Static Magnetic Field (T) | 1.5 | 1.5 | 1.5 | 1.5 |
| Pulse Sequence | T1-SE | T1-SE | GRE | GRE |
| TR (sec.) | 500 | 500 | 100 | 100 |
| TE (sec.) | 20 | 20 | 15 | 15 |
| Flip Angle | N/A | N/A | 30° | 30° |
| Bandwidth | 16 kHz | 16 kHz | 16 kHz | 16 kHz |
| Field of View | 30 cm | 30 cm | 30 cm | 30 cm |
| Matrix Size | 256 × 256 | 256 × 256 | 256 × 256 | 256 × 256 |
| Section Thickness | 5 mm | 5 mm | 5 mm | 5 mm |
| Maximum Readout Gradient Strength | 6.3 mT/m | 6.3 mT/m | 6.3 mT/m | 6.3 mT/m |
| Imaging Plane | parallel | perpendicular | parallel | perpendicular |
| Phantom Filler | gel | gel | gel | gel |

(T-1-SE, T1-weighted spin echo; GRE, gradient echo; N/A, not applicable; values for artifact size indicated in mm$^2$; Note that the T1 and T2 values for the gel used for the phantom filler are similar to the values of skeletal muscle or organ tissue.)

Example 25

A coating composition for PVC catheters was prepared as follows: a 3.2% solution of a polyether polyurethane-urea block copolymer available from CardioTech International, Inc. was prepared in a mixture of THF/alcohol in a 75/25 ratio by weight. A 4.0% solution of Polyvinyl chloride (PVC) was then prepared in THF. The two solutions were then combined in amounts that provide a 50/50 ratio by weight of the two polymers in solution. A sufficient quantity of 10% silver nitrate (AgNO$_3$) solution in water was then added to the polyurethane-urea/PVC polymer solution to produce a final silver concentration of approximately 5%, based on coating solids in the solution. A 2% sodium chloride solution in water was added to the coating solution in an amount sufficient to react with 100% of the AgNO$_3$ to produce a colloid of the poorly water soluble salt AgCl from all of the AgNO$_3$. The NaCl solution was added slowly to the polymer solution with stirring, and the solution began to turn cloudy with the formation of the fine colloidal AgCl. The amount of water in the final coating solution was about 4.8% of the total solvent weight. The amount of alcohol in the solution was about 13.3% of the total solvent weight. A PVC endotracheal tube was then coated by dipping it into the coating composition, followed by drying using standard methods. The tube was dipped to within about 4 cm from the end that resides outside the patient. The finished coating contained only the poorly water soluble, and therefore slow releasing, AgCl to provide primarily surface antimicrobial activity and limit the amount of silver released that could find its way into the lungs.

Finally, it will be understood that the preferred embodiments have been disclosed by way of example, and that other modifications may occur to those skilled in the art without departing from the scope and spirit of the appended claims.

What is claimed is:

1. An article comprising a substrate, a base coat on at least a portion of the substrate, and a top coat on at least a portion of the base coat, the top coat comprising a polyurethane, a polyurethane-urea-silane copolymer other than the polyurethane, and at least one oligodynamic metal compound.

2. The article of claim 1 wherein the article comprises a medical device.

3. The article of claim 2 wherein the medical device is chosen from catheters, cannulae, stents, guide wires, implant devices, contact lenses, IUDs, peristaltic pump chambers, endotracheal tubes, gastroenteric feeding tubes, arteriovenous shunts, condoms, oxygenator and kidney membranes, gloves, pacemaker leads, or wound dressings.

4. The article of claim 1 wherein the top coat comprises a dry elastic coating.

5. The article of claim 4 wherein the top coat is capable of becoming lubricious when wet.

6. The article of claim 1 wherein the polyurethane is chosen from polyether polyurethanes, polyester polyurethanes, polyurethaneureas, or their copolymers.

7. The article of claim 1 wherein the oligodynamic metal compound comprises at least one silver compound.

8. The article of claim 7 wherein the at least one silver compound comprises silver nitrate and colloidal silver chloride.

9. The article of claim 7 wherein the polyurethane is chosen from polyether polyurethanes, polyester polyurethanes, polyurethaneureas, or their copolymers.

10. The article of claim 9 wherein the article comprises a medical device chosen from catheters, cannulae, stents, guide wires, implant devices, contact lenses, IUDs, peristaltic pump chambers, endotracheal tubes, gastroenteric feeding tubes, arteriovenous shunts, condoms, oxygenator and kidney membranes, gloves, pacemaker leads, or wound dressings.

11. The article of claim 7 wherein the at least one oligodynamic metal compound is present in an amount between about 25 and about 50 μg/cm$^2$.

12. The article of claim 7 wherein the at least one oligodynamic metal compound is present in an amount between about 20 and about 30 μg/cm$^2$.

13. The article of claim 7 wherein the at least one oligodynamic metal compound is present in an amount between about 10 and about 20 μg/cm$^2$.

14. The article of claim 7 wherein the at least one oligodynamic metal compound is present in an amount between about 5 and about 15 μg/cm$^2$.

* * * * *

UNITED STATES PATENT AND TRADEMARK OFFICE
CERTIFICATE OF CORRECTION

| | |
|---|---|
| PATENT NO. | : 7,378,156 B2 |
| APPLICATION NO. | : 11/625038 |
| DATED | : May 27, 2008 |
| INVENTOR(S) | : Terry |

It is certified that error appears in the above-identified patent and that said Letters Patent is hereby corrected as shown below:

At column 1, line 7 of the printed patent, after "continuation" delete "on".

At column 15, line 2 of the printed patent, "biguamide" should be --biguanide--.

At column 15, line 6 of the printed patent, "biguamide" should be --biguanide--.

At column 16, line 20 of the printed patent, "aztneonam" should be --aztreonam--.

At column 17, line 14 of the printed patent, "iohexyl" should be --iohexol--.

At column 17, line 57 of the printed patent, "biguamide" should be --biguanide--.

At column 21, line 66 of the printed patent, "Polyarethanes" should be --Polyurethanes--.

At column 26, line 45 of the printed patent, "is" should be --are--.

At column 29, line 15 of the printed patent, "popodermatitis" should be --pododermatitis--.

At column 36, line 42 of the printed patent, "NR860" should be --NR 860--.

At column 39, line 55 of the printed patent, "cfU/g" should be --cfu/g--.

UNITED STATES PATENT AND TRADEMARK OFFICE
CERTIFICATE OF CORRECTION

PATENT NO. : 7,378,156 B2
APPLICATION NO. : 11/625038
DATED : May 27, 2008
INVENTOR(S) : Terry It is certified that error appears in the above-identified patent and that said Letters Patent is hereby corrected as shown below:

At column 42, line 44 of the printed patent, "sties" should be --sites--.

Signed and Sealed this

Second Day of September, 2008

JON W. DUDAS
*Director of the United States Patent and Trademark Office*